(12) United States Patent
Wimberly

(10) Patent No.: US 12,721,549 B1
(45) Date of Patent: Sep. 1, 2026

(54) WEARABLE MEDICAL MONITORING DEVICE WITH MICRONEEDLE ARRAY AND ARTIFICIAL INTELLIGENCE (AI)-BASED HEALTH ANOMALY DETECTION

(71) Applicant: EURISKO BIOSCIENCES LLC, Tallahassee, FL (US)

(72) Inventor: David Wimberly, Tallahassee, FL (US)

(73) Assignee: EURISKO BIOSCIENCES LLC, Tallahassee, FL (US)

( * ) Notice: Subject to any disclaimer, the term of this patent is extended or adjusted under 35 U.S.C. 154(b) by 0 days.

(21) Appl. No.: 19/446,855

(22) Filed: Jan. 12, 2026

(51) Int. Cl.
*A61B 5/145* (2006.01)
*A61B 5/00* (2006.01)
(Continued)

(52) U.S. Cl.
CPC ........ *A61B 5/14514* (2013.01); *A61B 5/0004* (2013.01); *A61B 5/14542* (2013.01);
(Continued)

(58) Field of Classification Search
CPC .............. A61B 5/0004; A61B 5/14514; A61B 5/14542; A61B 5/14546; A61B 5/1459;
(Continued)

(56) References Cited

U.S. PATENT DOCUMENTS

2008/0287830 A1 11/2008 Voeller
2020/0124519 A1 4/2020 Javanmard et al.
(Continued)

FOREIGN PATENT DOCUMENTS

IN 202411085456 A 12/2024
IN 202521007192 A 3/2025
(Continued)

OTHER PUBLICATIONS

Abbas Furniturewalla, Fully integrated wearable impedance cytometry platform on flexible circuit board with online smartphone readout, https://sci-hub.red/https:/www.nature.com/articles/s41378-018-0019-0, Jul. 30, 2018.

(Continued)

*Primary Examiner* — Jennifer Robertson
*Assistant Examiner* — Nidhi N Patel
(74) *Attorney, Agent, or Firm* — HULSEY P.C.

(57) ABSTRACT

A wearable medical monitoring device comprises a microneedle array configured to extract interstitial or capillary fluid from a user, biosensors configured to detect biomarkers including glucose and complete blood count parameters such as white blood cells, red blood cells, hemoglobin, hematocrit, and platelet count, a microprocessor configured to generate biomarker data from biosensor signals, and a wireless communication module configured to transmit biomarker data to a user device for forwarding to a server. The server analyzes biomarker data using machine learning models including time-series forecasting, anomaly detection, classification, and ensemble models to detect health condition anomalies and generate alerts. The machine learning models are updated via federated learning using anonymized data. The server establishes personalized baseline values and dynamically adjusts alert thresholds based on user-specific factors and environmental context.

16 Claims, 7 Drawing Sheets

(51) Int. Cl.
*A61B 5/1459* (2006.01)
*A61B 5/1473* (2006.01)
*G16H 10/40* (2018.01)
*G16H 15/00* (2018.01)

(52) U.S. Cl.
CPC ........ *A61B 5/14546* (2013.01); *A61B 5/1459* (2013.01); *A61B 5/1473* (2013.01); *A61B 5/7267* (2013.01); *A61B 5/746* (2013.01); *G16H 10/40* (2018.01); *G16H 15/00* (2018.01); *A61B 2560/0214* (2013.01); *A61B 2560/0238* (2013.01); *A61B 2560/0247* (2013.01)

(58) Field of Classification Search
CPC ..... A61B 5/1473; A61B 5/7267; A61B 5/746; A61B 2560/0214; A61B 2560/0238; A61B 2560/0247; G16H 10/40; G16H 15/00
See application file for complete search history.

(56) References Cited

U.S. PATENT DOCUMENTS

| | | | | |
|---|---|---|---|---|
| 2022/0068453 | A1* | 3/2022 | Simpson | A61B 5/7435 |
| 2023/0012662 | A1* | 1/2023 | Tehrani | A61B 5/14503 |
| 2023/0114479 | A1 | 4/2023 | Nyers et al. | |
| 2024/0032827 | A1 | 2/2024 | Durr et al. | |
| 2024/0206755 | A1 | 6/2024 | Shreim et al. | |
| 2024/0374169 | A1* | 11/2024 | Wu | A61B 5/1459 |
| 2025/0014731 | A1* | 1/2025 | Soori-Arachi | A61B 5/0022 |
| 2025/0144291 | A1* | 5/2025 | Dave | A61M 5/16804 |
| 2026/0024637 | A1* | 1/2026 | Elnady | G06V 30/14 |

FOREIGN PATENT DOCUMENTS

| | | | |
|---|---|---|---|
| IN | 202511028237 | A | 4/2025 |
| IN | 202541047952 | A | 6/2025 |
| IN | 202511061987 | A | 7/2025 |
| IN | 202541059383 | A | 7/2025 |

OTHER PUBLICATIONS

Malasaga, Elisa V.; Complete Blood Count (CBC) Analysis Mobile Application, https://sci-hub.red/https:/ieeexplore.ieee.org/document/9731857, 2021.

Trinity Biotech; Trinity Biotech Unveils CGM+: An AI-Native Platform Targeting the $260 Billion AI Wearable Market, https://www.trinitybiotech.com/wp-content/uploads/2025/07/Trinity-Biotech-Unveils-CGM-An-AI-Native-Platform-Targeting-the-260-Billion-AI-Wearable-Market.pdf, Jul. 24, 2025.

* cited by examiner

WEARABLE MEDICAL MONITORING DEVICE WITH MICRONEEDLE ARRAY AND ARTIFICIAL INTELLIGENCE (AI)-BASED HEALTH ANOMALY DETECTION

BACKGROUND OF THE INVENTION

Field of Invention

The present disclosure relates to wearable health monitoring devices, and more particularly to a wearable medical monitoring device comprising a microneedle array for extracting interstitial or capillary fluid, biosensors for detecting biomarkers, and a wireless communication module for transmitting biomarker data to a server configured to analyze the data using machine learning models to detect health anomalies and generate alerts.

Description of the Prior Art

Wearable health monitoring technologies have advanced considerably in recent years, with devices such as continuous glucose monitors (CGMs) gaining widespread adoption for tracking metabolic parameters. These devices typically adhere to the skin and utilize minimally invasive sensing mechanisms to access interstitial or capillary fluid for analysis. The complete blood count (CBC), which includes parameters such as white blood cell count, red blood cell count, hemoglobin, hematocrit, and platelet count, represents one of the most commonly ordered laboratory panels in clinical medicine and provides information relevant to detecting infections, anemia, immune system disorders, and other physiological conditions. The ability to continuously monitor multiple biomarkers simultaneously would provide a more comprehensive view of an individual's physiological status than current single-parameter monitoring approaches.

The physiological basis of biomarker monitoring relies on accessing biological fluids that contain measurable concentrations of clinically relevant analytes. Interstitial fluid, located within the dermis layer of the skin, contains biomarkers that correlate with blood concentrations and can be accessed through minimally invasive microneedle arrays that penetrate the epidermis without reaching deeper vascular structures. This approach enables continuous or periodic sampling without the discomfort and infection risks associated with traditional venipuncture, making it suitable for extended monitoring periods in non-clinical settings.

Existing wearable monitoring devices are generally limited to tracking a single biomarker, such as glucose, and do not provide multi-parameter analysis capabilities. Currently, obtaining CBC data requires periodic blood draws performed by medical professionals using laboratory equipment, which limits how frequently such measurements can be obtained and restricts continuous monitoring outside of clinical settings. Furthermore, many current systems lack seamless integration with clinical workflows, making it difficult to forward actionable data to healthcare providers in real time. Existing wearable devices often present raw or minimally processed data to users without sophisticated interpretation, predictive modeling, or intervention triggers.

Artificial intelligence and machine learning technologies have progressed rapidly in the field of medical diagnostics, offering capabilities for pattern recognition, anomaly detection, and predictive modeling based on physiological data. However, integration of such intelligent analysis systems with wearable health monitoring devices remains limited. Certain populations face particular challenges in accessing timely medical diagnostics due to geographic, environmental, or operational constraints. Individuals in remote locations, those operating in isolated environments such as spacecraft or submarines, elderly individuals managing chronic conditions, and populations in medically underserved areas may experience delays in obtaining laboratory results or accessing healthcare professionals.

One example is disclosed in a U.S. Publication No. 20200124519, entitled "Wearable impedance cytometer" ("the '519 Publication"). The '519 Publication discloses an impedance cytometer which includes a carrier that can be attached to a living being, with a biosensor mounted thereto. The biosensor includes a microfluidic flow channel, formed in the carrier, and an impedance circuit. The microfluidic flow channel accommodates passage of a particle therethrough. The impedance circuit, connected to the microfluidic flow channel, includes a signal generator that produces a high-frequency drive signal applied to the flow channel to produce a biosensor output signal having high-frequency variation resulting from the drive signal and low-frequency variation resulting from impedance variation within the flow channel during the particle's passage. A lock-in amplifier is disposed to (i) amplify the biosensor output signal, (ii) mix the amplified signal with the drive signal, and (iii) frequency-filter the mixed, amplified signal to output an impedance signal representing the low-frequency impedance variation resulting from the passage of the particle. Embodiments enable wearable, personalized cytometry.

Another example is disclosed in a U.S. Publication No. 20240206755, entitled "Systems and methods for determination of personalized health status predictions through precision medicine" ("the '755 Publication"). The '755 Publication discloses systems and methods directed to the personalization of machine learning models configured to generate patient health-related predictions for a patient wearing a biosensing device. The biosensing device may be mounted over or proximate to a vessel of a patient enabling biosensing data to be obtained or captured by the biosensing device. Particular implementations of the disclosure are directed to training a machine learning model to generate patient health-related predictions for a patient and retraining the machine learning model over time using data captured by the biosensing device worn by the patient to personalize the machine learning model to the individual patient. As a result, the personalized machine learning model enables the provision of precision medicine through the tailoring of the historical data on which the machine learning is trained.

Although the above discussed disclosures provide advancements in wearable biosensing and personalized health prediction, they still have problems and present incomplete solutions. Current devices lack the capability to simultaneously monitor multiple biomarkers including both glucose and complete blood count parameters in a single wearable form factor. The existing solutions do not adequately address the need for integrated artificial intelligence-based analysis that can detect anomalies, perform time-series forecasting, and generate predictive health alerts based on continuous multi-biomarker data streams. Additionally, many current devices lack seamless integration with healthcare provider workflows, failing to provide mechanisms for transmitting urgent alerts, AI-annotated clinical summaries, and trend data to designated healthcare personnel in real time.

Therefore, there is a need in the art to provide an improved wearable health monitoring system that can track multiple biomarkers continuously using a microneedle array, integrate with artificial intelligence-based analysis platforms for anomaly detection and predictive modeling, and facilitate communication of health data and alerts to both users and healthcare providers.

SUMMARY OF THE INVENTION

It is an object of the present invention to provide a wearable medical monitoring device comprising a microneedle array configured to extract interstitial or capillary fluid from a user, a plurality of biosensors configured to detect a plurality of biomarkers from the extracted fluid and a wireless communication module configured to transmit the biomarker data to a user device for forwarding to a server.

It is another object of the present invention to provide a server configured to analyze the biomarker data using one or more machine learning models including at least one of a time-series forecasting model, an unsupervised anomaly detection model, a classification model for risk scoring, or an ensemble model, to detect anomalies indicative of health conditions and to generate a health alert based on a detected anomaly.

It is another object of the present invention to provide a wearable device that uses a sensor attached to the skin and monitors over fifty items in the Complete Blood Count and additional markers totaling more than sixty biomarkers, including prostate-specific antigen (PSA) for men and heavy metals such as Arsenic, Cadmium, Cobalt, and Mercury.

It is another object of the present invention to provide a plurality of biosensors comprising an electrochemical sensor configured to detect glucose and an optical biosensor configured to detect hemoglobin levels using absorbance or scattering properties.

It is another object of the present invention to provide a microneedle array comprising microneedles measuring approximately 500-900 micrometers in length, and a battery configured to provide power to the microprocessor and the wireless communication module, wherein the wearable medical monitoring device is configured for continuous operation for a period of up to thirty days without replacement.

It is another object of the present invention to provide a time-series forecasting model comprising a Long Short-Term Memory neural network configured to detect rate-of-change metrics for each biomarker and to predict biomarker trajectory based on detected trends.

In order to overcome the limitations stated herein, the present invention provides a wearable medical monitoring device, a method for continuous health monitoring, and a health monitoring system. The wearable medical monitoring device comprises a microneedle array configured to extract interstitial or capillary fluid from a user, a plurality of biosensors configured to detect a plurality of biomarkers from the extracted fluid including glucose and at least one complete blood count parameter selected from a group consisting of white blood cells, red blood cells, hemoglobin, hematocrit, and platelet count, a microprocessor coupled to the plurality of biosensors and configured to generate biomarker data based on signals received from the plurality of biosensors, and a wireless communication module coupled to the microprocessor and configured to transmit the biomarker data to a user device for forwarding to a server. The server is configured to analyze the biomarker data using one or more machine learning models including at least one of a time-series forecasting model, an unsupervised anomaly detection model, a classification model for risk scoring, or an ensemble model, to detect anomalies indicative of health conditions and to generate a health alert based on a detected anomaly, wherein the one or more machine learning models are configured to be updated via federated learning using anonymized data.

In one aspect, the health monitoring system employs a multi-tiered artificial intelligence architecture comprising an edge layer, a gateway layer, a cloud analytics layer, and an alerting and triage layer. The edge layer is implemented on the wearable medical monitoring device and comprises the microprocessor configured to perform basic signal conditioning and pre-processing of biosensor signals using low-power computational resources. The gateway layer comprises the first user device configured to serve as an encrypted data conduit and intermediary between the wearable medical monitoring device and cloud services, wherein the first user device forwards the biomarker data to the server via the network using secure communication protocols. The cloud analytics layer is implemented on the server and comprises the one or more machine learning models configured to perform pattern recognition, anomaly detection, predictive modeling, and patient-specific diagnostics based on the received biomarker data. The alerting and triage layer is implemented on the server and is configured to determine when analysis results should trigger user alerts transmitted to the first user device, physician notifications transmitted to the second user device, or emergency escalations based on the severity and urgency of detected anomalies.

In one aspect, the method for continuous health monitoring comprises extracting, by a microneedle array of a wearable device adhered to skin of a user, interstitial or capillary fluid from the user, detecting, by a plurality of biosensors of the wearable device, a plurality of biomarkers from the extracted fluid wherein the plurality of biomarkers comprises glucose and at least one complete blood count parameter, generating, by a microprocessor of the wearable device, biomarker data based on signals from the plurality of biosensors, transmitting, by a wireless communication module of the wearable device, the biomarker data to a user device, forwarding, by the user device, the biomarker data to a server via a network, analyzing, by the server, the biomarker data using one or more machine learning models including at least one of a time-series forecasting model using Long Short-Term Memory neural networks, an unsupervised anomaly detection model, a classification model for risk scoring, or an ensemble model, to detect anomalies indicative of health conditions, wherein the one or more machine learning models are configured to be updated via federated learning using anonymized data, and generating, by the server, a health alert based on a detected anomaly.

In another aspect, analyzing the biomarker data using the one or more machine learning models comprises applying the time-series forecasting model using Long Short-Term Memory neural networks to detect rate-of-change metrics for each biomarker. The method further comprises predicting, by the server, a biomarker trajectory based on the detected rate-of-change metrics and generating a predictive health alert with an estimated time to threshold crossing when the predicted trajectory crosses a clinical threshold.

In yet another aspect, the method further comprises collecting, by the server, initial biomarker readings over a calibration period, establishing, by the server, individualized baseline values for the at least one complete blood count parameter based on the initial biomarker readings, and adjusting, by the server, alert thresholds based on user-specific factors including age, sex, and known medical conditions. The method further comprises detecting, by the server, an environmental context change based on environmental data received from the user device, and dynamically updating, by the server, the alert thresholds based on the detected environmental context change.

In another aspect, the method further comprises classifying, by the server, the detected anomaly by priority level, transmitting, by the server, an immediate alert to a healthcare personnel device when the detected anomaly is classified as high priority, and providing, by the server, an artificial intelligence (AI)-annotated clinical summary along with trend graphs to the healthcare personnel device. Classifying the detected anomaly by priority level comprises assigning the detected anomaly to one of a low priority level for non-urgent deviations, a moderate priority level for significant but non-immediate issues, and a high priority level for acute changes with potential for rapid deterioration.

In another aspect, the health monitoring system comprises a wearable medical monitoring device configured to be adhered to skin of a user, the wearable medical monitoring device including a microneedle array configured to extract interstitial or capillary fluid from the user, a plurality of biosensors configured to detect a plurality of biomarkers including glucose and at least one complete blood count parameter from the extracted fluid, a microprocessor configured to generate biomarker data based on signals from the plurality of biosensors, and a wireless communication module configured to transmit the biomarker data. The health monitoring system further comprises a first user device configured to receive the biomarker data from the wearable medical monitoring device and to forward the biomarker data via a network, and a server configured to receive the biomarker data from the first user device, to analyze the biomarker data using one or more machine learning models including at least one of a time-series forecasting model, an unsupervised anomaly detection model, a classification model for risk scoring, or an ensemble model, to detect anomalies indicative of health conditions, and to generate a health alert based on a detected anomaly, wherein the one or more machine learning models are configured to be updated via federated learning using anonymized data.

In yet another aspect, the health monitoring system further comprises a second user device configured to be operated by healthcare personnel, wherein the server is configured to transmit the health alert to the second user device when the detected anomaly is classified as high priority. The server is configured to provide an artificial intelligence (AI)-annotated clinical summary to the second user device, the AI-annotated clinical summary including trend graphs and suggested ICD-10 codes corresponding to the detected anomaly. The server is further configured to establish individualized baseline values for the at least one complete blood count parameter based on initial biomarker readings collected over a calibration period and to adjust alert thresholds based on user-specific factors derived from user profile data.

In one advantageous feature of the present invention, the wearable medical monitoring device provides continuous 24/7 biomarker analysis, eliminating the need for users to wait months or years between periodic blood draws to receive vital health information, thereby detecting health anomalies and biomarker trends in real time and enabling early intervention for conditions that would otherwise remain undetected until the next scheduled blood draw.

In another advantageous feature of the present invention, the microneedle array comprises microneedles measuring approximately 500-900 micrometers in length, which is sufficient to penetrate the stratum corneum and reach interstitial fluid or shallow capillary beds while remaining short enough to avoid stimulating pain receptors, thereby enabling minimally invasive fluid extraction with minimal discomfort to the user.

In another advantageous feature of the present invention, the server is configured to build a dynamic health profile for each user that establishes individualized baselines for complete blood count parameters and adjusts alert thresholds based on age, sex, known conditions, and environmental context, thereby minimizing false positives while preserving sensitivity to early-stage changes specific to each user.

In another advantageous feature of the present invention, the one or more machine learning models include rate-of-change detectors that trigger alerts even if absolute biomarker values remain within normal limits, enabling detection of rapidly evolving health conditions before biomarker values reach abnormal ranges.

In another advantageous feature of the present invention, the wearable medical monitoring device includes microfluidic channels configured to transport fluid from the microneedle array to sensor chambers, wherein the microfluidic channels include anti-clotting surfaces that are heparin-coated to prevent sensor fouling and maintain fluid flow over extended operation periods.

In another advantageous feature of the present invention, the server is configured to perform multi-variable pattern detection to identify complex combinations of biomarker changes associated with specific health risks, including detecting a combination of rising white blood cell count, increasing temperature, and falling hematocrit that suggests sepsis, even when individual biomarker values remain within normal ranges.

In another advantageous feature of the present invention, the wearable medical monitoring device includes temperature and pH compensation modules configured to normalize readings from the plurality of biosensors, thereby improving measurement accuracy across varying physiological and environmental conditions.

In another advantageous feature of the present invention, the health monitoring system supports integration with health systems through Fast Healthcare Interoperability Resources (FHIR) and Health Level Seven (HL7) standards, allowing direct embedding of biomarker data into Electronic Health Records (EHRs) and reducing delays between anomaly detection and clinical evaluation.

DETAILED DESCRIPTION OF THE PREFERRED EMBODIMENT

The following description sets forth exemplary aspects of the present disclosure. It should be recognized, however, that such description is not intended as a limitation on the scope of the present disclosure. Rather, the description also encompasses combinations and modifications to those exemplary aspects described herein.

A detailed description of systems, devices, and methods consistent with embodiments of the present disclosure is provided below. While several embodiments are described, it should be understood that disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments can be practiced without some or all of these details. Moreover, for the purpose of clarity, certain technical material that is known in the related art has not been described in detail in order to avoid unnecessarily obscuring the disclosure.

Figure 1:
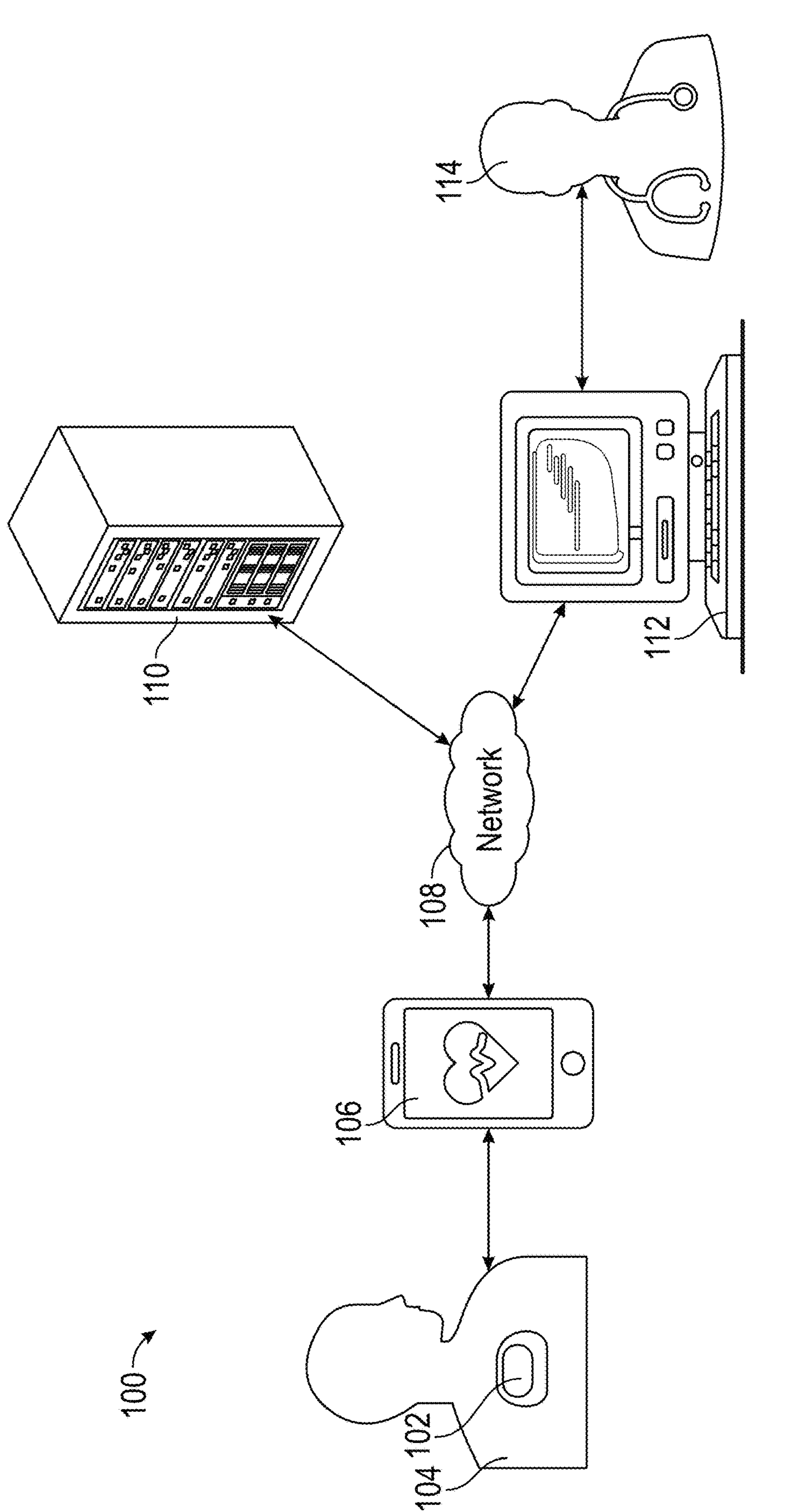
FIG. 1 illustrates a block diagram of a health monitoring system, in accordance with one embodiment of the present invention.

Referring to FIG. 1, a health monitoring system 100 configured for continuous multi-biomarker monitoring and artificial intelligence (AI)-based analysis is shown, in accordance with one exemplary embodiment of the present invention. Health monitoring system 100 includes a wearable medical monitoring device 102 (or wearable device 102), a first user device 106, a server 110, and a second user device 112. A user 104 operates first user device 106 to receive biomarker data from wearable medical monitoring device 102 and to access health monitoring information and alerts. First user device 106 communicates with server 110 via a network 108 to forward biomarker data for analysis and to retrieve processed results, trend data, and health alerts generated by server 110. A healthcare personnel 114 operates second user device 112 to monitor patient health status and respond to detected anomalies. Second user device 112 communicates with server 110 via network 108 to access biomarker data, AI-annotated clinical summaries, and urgent alerts associated with user 104. In some cases, healthcare personnel 114 may access server 110 through second user device 112 to configure alert thresholds, review historical trend data, and manage care assignments for multiple users.

Here, user 104 refers to a patient or an individual interested in receiving updates on health anomalies. Wearable medical monitoring device 102 is configured to attach to user 104 in a variety of form factors. In some embodiments, wearable medical monitoring device 102 comprises a patch that adheres directly to the skin of user 104, with the patch incorporating biocompatible and hypoallergenic materials to minimize skin irritation during extended wear periods. In other embodiments, wearable medical monitoring device 102 is a removable device that attaches to user 104 via an adhesive layer, allowing for easy removal and reattachment while maintaining secure contact with the skin surface. In some cases, the adhesive layer may be designed to be waterproof and sweat-resistant, enabling wearable medical monitoring device 102 to remain securely attached during physical activities and in diverse environmental conditions. The form factor of wearable medical monitoring device 102 is compact and designed to be inconspicuous during wear, with dimensions comparable to existing continuous glucose monitor sensors.

Wearable medical monitoring device 102 is attached to various anatomical locations on user 104 depending on monitoring requirements and user preferences. In some embodiments, wearable medical monitoring device 102 is positioned on the upper arm, which provides a stable attachment site with relatively consistent interstitial fluid access. In other embodiments, wearable medical monitoring device 102 is attached to the abdomen, thigh, lower back, or other body regions where subcutaneous tissue depth and skin characteristics are suitable for microneedle penetration and fluid extraction. The selection of attachment location is influenced by factors such as the specific biomarkers being monitored, the user's activity level, clothing considerations, and individual anatomical variations. In some cases, healthcare personnel 114 may recommend a particular attachment site based on clinical requirements or the user's medical history. The flexibility in attachment location allows wearable medical monitoring device 102 to accommodate users with different body types, mobility constraints, or occupational requirements that may preclude attachment at certain anatomical sites.

Wearable medical monitoring device 102 is attached to user 104, enabling wearable medical monitoring device 102 to interface with user 104 for biomarker data collection. Wearable medical monitoring device 102 is also connected to first user device 106, which receives biomarker data transmitted wirelessly from wearable medical monitoring device 102. In some implementations, user 104 operates first user device 106. First user device 106 indicates an electronic device such as a smartphone, tablet computer, personal digital assistant, laptop computer, desktop computer, smart watch, and the like. In some cases, first user device 106 is a smartphone running a mobile application configured to receive, display, and forward biomarker data from wearable medical monitoring device 102.

With continued reference to FIG. 1, first user device 106 communicatively connects to server 110 through network 108. As used herein, the term "network" refers to a communication infrastructure that facilitates data transmission, protocol routing, and connectivity services between server 110 components and external devices through various networking technologies including wireless networks, cellular networks, internet protocols, and local area networks. Network 108 includes a wireless network, a wired network, or a combination thereof. Network 108 is implemented as one of the different types of networks, such as intranet, local area network (LAN), wide area network (WAN), the Internet, cellular networks, and the like. Network 108 is implemented as a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Network 108 implements multiple communication protocols including Wi-Fi standards, cellular data networks such as 4G LTE and 5G, Bluetooth™ connectivity, and internet protocol suites that enable comprehensive connectivity options for different user devices and interaction scenarios. Further, network 108 includes a variety of network devices, including routers, bridges, servers, computing devices, storage devices, and the like. Network 108 is connected to server 110, which receives and processes biomarker data forwarded from first user device 106. Server 110 performs analysis of the biomarker data using machine learning algorithms to detect anomalies indicative of health conditions. Server 110 is implemented as a single server or as a plurality of servers operating in a distributed configuration.

As further shown in FIG. 1, second user device 112 communicatively connects to server 110 via network 108. As specified above, healthcare personnel 114 operates the second user device 112. Healthcare personnel 114 accesses both data transmitted by first user device 106 and processed data from server 110 using second user device 112. Healthcare personnel 114 reviews the biomarker data and analysis results via second user device 112 and provides recommendations to user 104 based on the reviewed information. Healthcare personnel 114 is any individual who interacts with server 110 to monitor patient biomarker data, configure alert thresholds, or manage patient care assignments. Healthcare personnel 114 may also be a clinical administrator responsible for configuring and maintaining the monitoring system across a healthcare organization. Healthcare personnel 114 interacts with server 110 through second user device 112 or through direct interfaces provided by server 110. In some cases, second user device 112 is a web-based physician dashboard accessible through a computer or tablet device, enabling healthcare personnel 114 to monitor multiple patients, set escalation rules, and respond to urgent events remotely.

With continued reference to FIG. 1, health monitoring system 100 supports integration with health systems through Fast Healthcare Interoperability Resources (FHIR) and Health Level Seven (HL7) standards, allowing direct embedding of data into Electronic Health Records (EHRs). Health monitoring system 100 supports pairing of wearable medical monitoring device 102 with first user device 106 application using Radio-Frequency Identification (RFID) and Near-Field Communication (NFC) protocols to determine which devices can provide medical sensor data.

In some implementations, server 110 encrypts all data at rest using Advanced Encryption Standard (AES)-256 or higher encryption and secures data in transit using Transport Layer Security (TLS) 1.3 protocols with forward secrecy. Server 110 implements role-based access controls (RBAC) with multi-factor authentication (MFA) required for healthcare personal dashboards accessed through second user device 112. In some cases, server 110 digitally signs and versions each data packet to ensure integrity and non-repudiation.

Server 110 is supported by redundant databases, real-time failover systems, daily encrypted backups, and edge-caching to allow functionality to continue during temporary network disruptions. Health monitoring system 100 allows user 104 to view all stored data and analytics in real time through first user device 106, control what data is shared and with whom, revoke physician access at any time, and download or delete a full health record associated with user 104.

Figure 2:
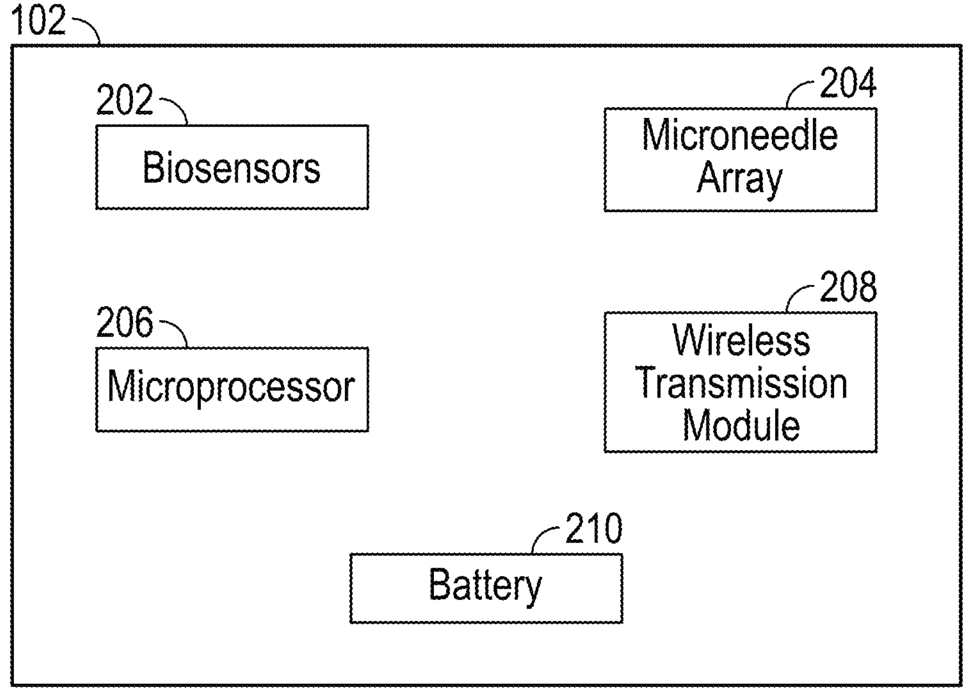
FIG. 2 illustrates a block diagram of a wearable medical monitoring device, in accordance with one embodiment of the present invention.

Referring to FIG. 2, a block diagram of wearable medical monitoring device 102, in accordance with one exemplary embodiment of the present invention. Wearable medical monitoring device 102 includes a biosensor 202, a microneedle array 204, a microprocessor 206, a wireless communication module 208, and a battery 210. Wearable medical monitoring device 102 is configured in a planar patch array that is adhered to the skin of user 104. The form factor of wearable medical monitoring device 102 is compact and comparable to a continuous glucose monitor (CGM) sensor, designed to be inconspicuous during wear. It should be understood that the patch configuration described herein is presented for illustrative purposes and is not intended to limit the scope of the invention. Various other form factors and configurations of wearable medical monitoring device 102 are contemplated and fall within the scope of the present invention.

With continued reference to FIG. 2, biosensor 202 is configured to detect biomarkers from fluid samples obtained through microneedle array 204. As used herein, the term "biosensor" may refer to one or more biosensors depending on the specific application requirements. For ease of reference, a single biosensor is described throughout this disclosure. However, it would be apparent to a person skilled in the art that multiple biosensors may be employed to sense different parameters as needed. Biosensor 202 comprises an electrochemical sensor for detecting glucose and lactate. In some cases, biosensor 202 comprises an aptamer-based sensor for detecting prostate-specific antigen (PSA), cytokines, or hormones. Biosensor 202 comprises an optical biosensor for cell counting, hemoglobin, and hematocrit levels using absorbance or scattering properties. In some cases, biosensor 202 comprises impedance-based sensors for cell morphology and concentration such as white blood cell (WBC) differentials.

As used herein, the term "biomarkers" may refer to measurable indicators of a biological state or condition detected from biological fluids, which may include, but are not limited to, glucose, hemoglobin A1c (HbA1c), prostate-specific antigen (PSA), complete blood count (CBC) parameters such as white blood cells (WBC), red blood cells (RBC), hemoglobin, hematocrit, and platelet count, as well as other molecular, biochemical, or physiological characteristics.

Further, biosensor 202 is configured to detect over fifty items in the CBC plus additional markers totaling more than sixty biomarkers. In some cases, biosensor 202 is configured to detect additional biomarkers including heavy metals such as Arsenic, Cadmium, Cobalt, and Mercury for workers in industrial settings such as astronauts, submariners, and shipyard workers.

In some cases, wearable medical monitoring device 102 has a modular architecture that allows for expansion to detect cardiac markers such as troponin and B-type natriuretic peptide (BNP), hormonal profiles such as cortisol, estrogen, and testosterone, infectious agents via antigen or antibody detection, and liver and kidney panels such as aspartate aminotransferase (AST), alanine aminotransferase (ALT), creatinine, and blood urea nitrogen (BUN).

Microneedle array 204 includes one or more microneedles configured to extract interstitial fluid 306 from user 104. The microneedles of microneedle array 204 are configured to penetrate through epidermis 302 and dermis 304 to access interstitial fluid 306 for biomarker analysis by biosensor 202. Microneedle array 204 is configured to extract interstitial or capillary fluid 306 from user 104 through minimally invasive penetration of the skin. Microneedle array 204 provides fluid samples to biosensor 202 for biomarker analysis. Microprocessor 206 receives signals from biosensor 202 and processes the biomarker data for transmission. Microprocessor 206 performs signal filtering, amplification, and analog-to-digital conversion of sensor outputs.

With continued reference to FIG. 2, wireless communication module 208 is coupled to microprocessor 206 and is configured to transmit the processed biomarker data to an external device such as first user device 106. Wireless communication module 208 utilizes Bluetooth™ Low Energy (BLE) for communication with first user device 106. In some cases, wireless communication module 208 may alternatively utilize Zigbee™ or LoRa™ protocols for communication. Wireless communication module 208 includes a Radio-Frequency Identification (RFID) radio frequency circuit allowing for RF communication using Near-Field Communication (NFC) protocol. The NFC circuit powers wearable medical monitoring device 102 when communicating with first user device 106, with battery 210 providing additional power for readings. Wireless communication module 208 provides connectivity to first user device 106, enabling wearable medical monitoring device 102 to communicate with external systems and devices. Wireless communication module 208 supports concurrent multiple communication technologies.

Battery 210 provides power to the components of wearable medical monitoring device 102. Battery 210 comprises a thin-film battery or an energy-harvesting unit such as a thermoelectric unit. In some embodiments, battery 210 is provided as a battery strip. The battery strip is integrated with microneedle array 204 or positioned adjacent to microneedle array 204. Wearable medical monitoring device 102 starts up when biosensor 202 is inserted into a sensor disc completing a circuit, saving battery power for longer operation.

With continued reference to FIG. 2, wearable medical monitoring device 102 is designed to be worn for up to thirty consecutive days without requiring removal, recharging, or calibration. Wearable medical monitoring device 102 includes an adhesive patch made from biocompatible, hypoallergenic materials. Wearable medical monitoring device 102 is designed to be waterproof and sweat-resistant, enabling use in extreme physical conditions and diverse environmental settings.

Wearable medical monitoring device 102 includes onboard data caching and delayed-sync mechanisms allowing wearable medical monitoring device 102 to operate autonomously for days or weeks when network contact is unavailable, syncing when contact is re-established. Wearable medical monitoring device 102 includes self-diagnostic routines that monitor sensor degradation and notify user 104 and healthcare personnel 114 if readings become unreliable or if physical degradation is detected.

Figure 3:
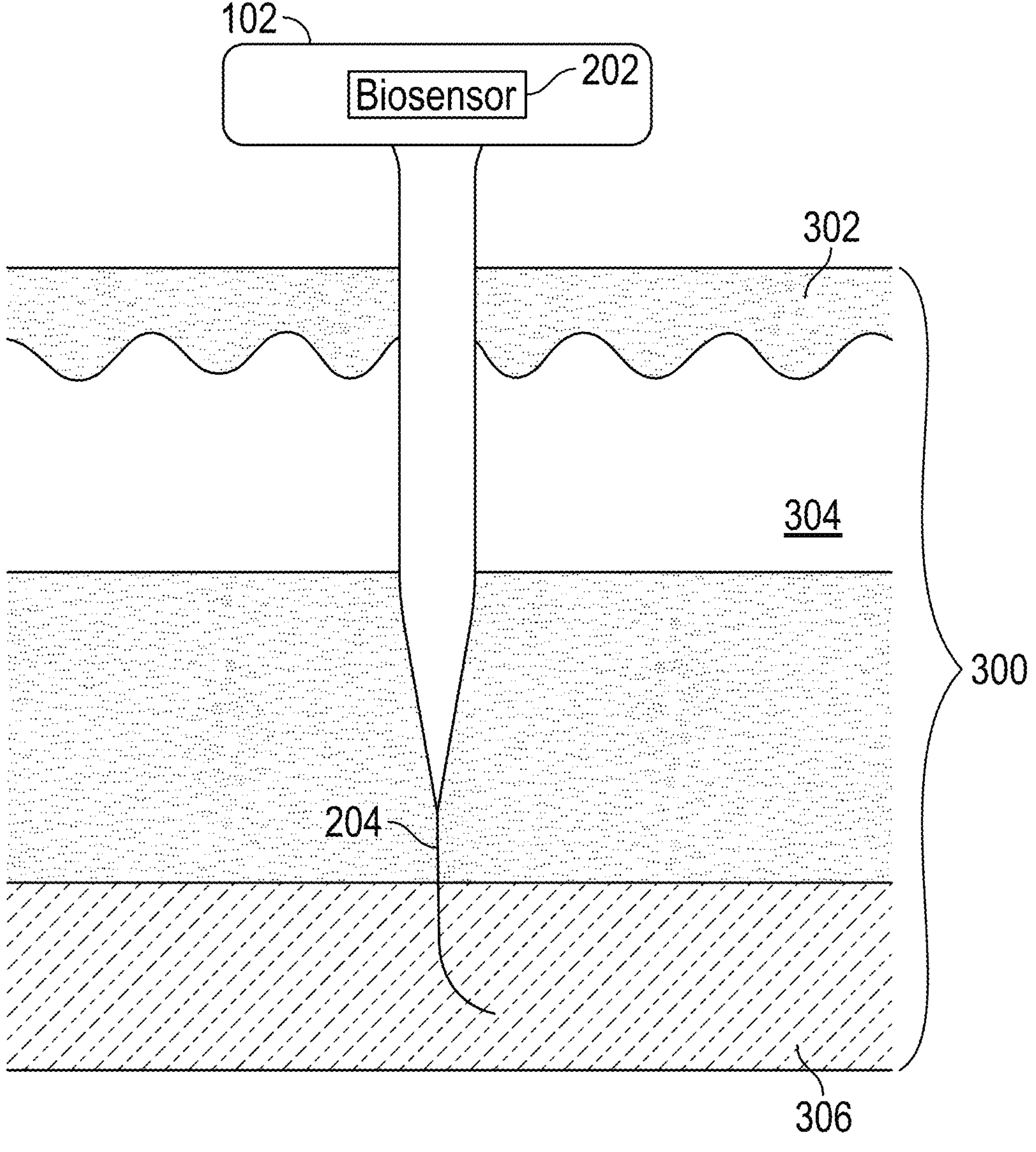
FIG. 3 illustrates a cross-sectional diagram showing an interface between the wearable medical monitoring device and layers of skin, in accordance with one embodiment of the present invention.

Referring to FIG. 3, a cross-sectional diagram showing wearable medical monitoring device 102 interfacing layers of skin 300 is shown, in accordance with one exemplary embodiment of the present invention. As known, layers of skin 300 include an epidermis 302, a dermis 304, and interstitial fluid 306. Epidermis 302 represents the outermost layer of the skin and includes the stratum corneum as the uppermost sublayer. Dermis 304 is positioned beneath epidermis 302 and contains blood vessels, nerve endings, and connective tissue. Interstitial fluid 306 is located within the deeper tissue layers and surrounds cells in dermis 304 and subcutaneous regions.

In accordance with the present invention, microneedle array 204 extends from wearable medical monitoring device 102 and penetrates through epidermis 302 and dermis 304 to access interstitial fluid 306. Microneedle array 204 comprises microneedles measuring approximately 500-900 micrometers (μm) in length. This length range is sufficient to penetrate the stratum corneum of epidermis 302 and reach interstitial fluid 306 or shallow capillary beds within dermis 304, while remaining short enough to avoid stimulating pain receptors located in deeper tissue structures. Microneedle array 204 thereby enables fluid extraction with minimal discomfort to user 104.

In some implementations, microneedle array 204 is fabricated from medical-grade silicon, polymers, or metallic alloys with biocompatible coatings. In some cases, microneedle array 204 is fabricated from silicon-coated arrays that prevent irritation while ensuring effective fluid sampling from interstitial fluid 306. The biocompatible materials of microneedle array 204 reduce infection risk due to the shallow penetration depth into layers of skin 300.

In one exemplary embodiment, wearable medical monitoring device 102 includes microfluidic channels configured to transport fluid from microneedle array 204 to sensor chambers containing biosensor 202. The microfluidic channels are fabricated through soft lithography techniques on polydimethylsiloxane (PDMS) or similar polymers. In some cases, the microfluidic channels are fabricated on other polymer substrates suitable for biomedical applications.

In one exemplary embodiment, wearable medical monitoring device 102 includes flow rectifiers within the microfluidic channels to ensure consistent sample delivery from interstitial fluid 306 to biosensor 202. The flow rectifiers maintain uniform fluid flow rates through the microfluidic channels regardless of variations in fluid viscosity or external pressure conditions.

In one exemplary embodiment, wearable medical monitoring device 102 includes anti-clotting surfaces within the microfluidic channels. The anti-clotting surfaces are heparin-coated to prevent sensor fouling and maintain fluid flow through the microfluidic channels over extended operation periods. The heparin coating inhibits coagulation of blood components that may be present in the extracted fluid samples from interstitial fluid 306.

In one exemplary embodiment, wearable medical monitoring device 102 includes temperature and pH compensation modules configured to normalize readings from biosensor 202. The temperature and pH compensation modules adjust sensor output values based on detected variations in fluid temperature and acidity levels, thereby improving measurement accuracy across varying physiological and environmental conditions.

In one exemplary embodiment, wearable medical monitoring device 102 uses capillary action to transport fluid through the microfluidic channels toward sensor chambers containing biosensor 202. In some cases, wearable medical monitoring device 102 may alternatively or additionally use low-power micro-pumps to transport fluid through the microfluidic channels. The capillary action or micro-pump transport mechanisms refresh biosensor 202 interface at regular intervals, allowing both continuous and periodic sampling of interstitial fluid 306 based on energy availability and analyte requirements.

In some cases, first user device 106 displays a tiered alert model comprising informational alerts for mild deviations, cautionary alerts for intermediate concerns with suggested actions, and critical alerts for high-risk trends or threshold crossings. Informational alerts notify user 104 of minor biomarker variations that do not require immediate action but may warrant monitoring. Cautionary alerts provide user 104 with behavioral recommendations and symptom checklists in response to biomarker patterns suggesting intermediate health concerns. Critical alerts notify user 104 of biomarker patterns indicating potential health emergencies and include instructions for seeking medical attention. The tiered alert model reduces alarm fatigue by reserving high-urgency notifications for situations requiring immediate user attention.

First user device 106 includes a secure physician forwarding feature enabling user 104 or server 110 autonomously to send data packets including trend summaries, PDF clinical reports, raw data exports in CSV or FHIR-compatible formats, and timestamped anomaly logs to designated healthcare personnel 114. The physician forwarding feature encrypts data packets before transmission and verifies recipient authorization before delivering health information. User 104 may configure the physician forwarding feature to automatically transmit data packets when specific alert conditions are detected or may manually initiate data transmission through first user device 106 interface. The physician forwarding feature enables healthcare personnel 114 to receive comprehensive biomarker data and analysis results without requiring user 104 to manually compile and transmit health information.

In some cases, the AI analysis generated by server 110 is forwarded to an AI-based diagnostic device (not shown), referred to as a "doc-in-a-box device," for immediate discussion and treatment guidance. The AI-based diagnostic device provides user 104 with interactive consultation capabilities based on the biomarker analysis, enabling user 104 to receive preliminary diagnostic information and treatment recommendations in situations where healthcare personnel 114 are unavailable or when immediate guidance is needed. The forwarding of AI analysis to the AI-based diagnostic device occurs in addition to or as an alternative to forwarding to healthcare personnel 114, depending on user preferences and availability of medical professionals.

Second user device 112 provides healthcare personnel 114 access to a dedicated web-based physician dashboard including patient-specific trend dashboards, AI-annotated CBC and metabolic summaries, alert logs and anomaly flags, and clinical suggestions based on evidence-based protocols. The patient-specific trend dashboards display time-series visualizations of biomarker values for individual users over configurable time periods. The AI-annotated summaries highlight biomarker values that triggered machine learning model alerts and provide explanations for the alert classifications. The clinical suggestions recommend diagnostic tests, treatment modifications, or follow-up actions based on detected biomarker patterns and established clinical protocols.

Second user device 112 allows healthcare personnel 114 to set their own thresholds for alerts enabling alignment with a patient's known conditions or therapeutic goals. Healthcare personnel 114 configures patient-specific alert thresholds through the physician dashboard that override default threshold values established by server 110. The customizable thresholds enable healthcare personnel 114 to account for individual patient characteristics, ongoing treatments, or known medical conditions that affect normal biomarker ranges. Server 110 applies the healthcare personnel-configured thresholds when evaluating biomarker data for the associated user 104.

Server 110 classifies medical events into three escalation levels: low priority for non-urgent deviations logged silently or bundled into weekly reports, moderate priority for significant but non-immediate issues forwarded with suggested next steps, and high priority for acute changes with potential for rapid deterioration triggering immediate provider alert and patient notification. Low priority events are recorded in server 110 logs and aggregated into periodic summary reports delivered to healthcare personnel 114 through second user device 112. Moderate priority events generate notifications to healthcare personnel 114 with recommended actions and timeframes for follow-up. High priority events trigger immediate alerts to both user 104 through first user device 106 and healthcare personnel 114 through second user device 112, with escalation protocols activated if acknowledgment is not received within defined time periods.

Server 110 generates alerts that include confidence scores, supporting data visualizations, and suggested ICD-10 codes to assist with triage and documentation. The confidence scores indicate the statistical certainty of the detected anomaly based on machine learning model outputs and data quality metrics. The supporting data visualizations include trend graphs, comparison charts, and annotated biomarker timelines that provide context for the alert. The suggested ICD-10 codes facilitate clinical documentation and billing processes by providing standardized diagnostic codes associated with the detected biomarker patterns.

Server 110 includes explainability layers built into deep learning models to justify decisions and provide transparent AI inferences with logic trees. The explainability layers generate human-readable explanations for machine learning model outputs that describe which biomarker values and patterns contributed to alert classifications. The logic trees present decision pathways that led to specific risk scores or anomaly detections, enabling healthcare personnel 114 to evaluate the reasoning behind AI-generated alerts. The explainability features support clinical decision-making by providing healthcare personnel 114 with sufficient information to verify or override machine learning model recommendations.

Server 110 maintains audit trails that log every inference and decision for post-hoc review by healthcare professionals. The audit trails record timestamps, input biomarker values, model parameters, confidence scores, and output classifications for each machine learning inference performed by server 110. Healthcare personnel 114 accesses the audit trails through second user device 112 to review historical alert generation and model behavior for specific users. The audit trails support quality assurance processes, regulatory compliance requirements, and investigation of adverse health events by providing complete records of AI system behavior.

First user device 106 includes engagement features configured to promote long-term user adherence to health monitoring protocols. The engagement features comprise personalized health goals that are established based on user 104 health profile, medical history, and biomarker baseline values. User 104 sets target ranges for specific biomarkers through first user device 106 interface, and first user device 106 tracks progress toward achieving and maintaining biomarker values within the target ranges. The personalized health goals are adjusted over time based on changes in user 104 health status or recommendations from healthcare personnel 114.

First user device 106 includes gamified rewards for trend stabilization that provide positive reinforcement when user 104 maintains biomarker values within target ranges over defined time periods. The gamified rewards include achievement badges, progress indicators, streak counters, and milestone notifications displayed through first user device 106 interface. User 104 receives gamified rewards for maintaining glucose stability, achieving consistent CBC parameter values, or demonstrating improvement in previously elevated biomarker readings. The gamification features increase user engagement with health monitoring activities and encourage sustained adherence to treatment protocols and lifestyle modifications.

First user device 106 includes medication reminders configured to notify user 104 of scheduled medication administration times. The medication reminders are configured by user 104 or healthcare personnel 114 through first user device 106 interface and include dosage information, medication names, and administration instructions. First user device 106 correlates medication reminder acknowledgments with subsequent biomarker readings to assess medication effectiveness and adherence patterns. The medication reminders are synchronized with biomarker monitoring schedules to enable evaluation of medication effects on tracked health parameters.

First user device 106 includes contextual education modules that provide user 104 with information explaining CBC values, glucose control mechanisms, and interpretations of abnormal biomarker results. The contextual education modules are triggered in response to specific biomarker readings, alert conditions, or user queries through first user device 106 interface. The education content includes explanations of physiological processes, descriptions of health conditions associated with biomarker abnormalities, and guidance on lifestyle factors that may influence biomarker values. The contextual education modules improve user 104 health literacy and enable informed participation in health management decisions.

First user device 106 application allows configuration of when readings take place through a configurable reading schedule interface. User 104 specifies time intervals for biomarker sampling, designates specific times of day for readings, or configures event-triggered sampling based on activities such as meals or exercise. The configurable reading schedule enables user 104 to align biomarker monitoring with daily routines, medication schedules, or clinical monitoring requirements specified by healthcare personnel 114. First user device 106 transmits the configured reading schedule to wearable medical monitoring device 102, which adjusts sampling frequency and timing based on the received schedule parameters.

First user device 106 application allows configuration of limits on normal or high/low measurements to alert user 104. User 104 specifies upper and lower threshold values for individual biomarkers through first user device 106 interface, and first user device 106 generates alerts when biomarker readings exceed or fall below the configured limits. The configurable alert limits enable user 104 to customize notification sensitivity based on personal health goals, known medical conditions, or guidance from healthcare personnel 114. First user device 106 stores multiple threshold configurations for different biomarkers and applies different threshold values based on time of day, activity context, or other configurable conditions.

First user device 106 application includes auto-schedule telemedicine capabilities configured to initiate consultation scheduling in response to detected health anomalies. When server 110 detects biomarker patterns indicating a need for clinical consultation, first user device 106 automatically schedules a telemedicine appointment with designated healthcare personnel 114 based on availability information retrieved from healthcare provider scheduling systems. First user device 106 preloads the provider's dashboard accessible through second user device 112 with relevant findings including biomarker trend data, alert history, and AI-generated clinical summaries prior to the scheduled consultation. The auto-schedule telemedicine feature reduces delays between anomaly detection and clinical evaluation by initiating consultation scheduling without requiring manual intervention by user 104.

Second user device 112 provides healthcare personnel 114 access to a physician dashboard configured for monitoring multiple patients and managing clinical workflows. The physician dashboard displays summary views of patient populations showing alert status, recent biomarker trends, and priority rankings for clinical attention. Healthcare personnel 114 navigates from summary views to detailed patient records containing comprehensive biomarker histories, treatment notes, and communication logs. The physician dashboard supports filtering and sorting of patient lists based on alert severity, biomarker categories, or custom criteria defined by healthcare personnel 114.

Second user device 112 enables healthcare personnel 114 to configure customizable alert thresholds for individual patients that override default threshold values established by server 110. Healthcare personnel 114 adjusts threshold values for specific biomarkers based on patient medical history, ongoing treatments, or therapeutic goals. The customizable alert thresholds account for patient-specific factors such as chronic conditions, medication effects, or physiological variations that affect normal biomarker ranges. Server 110 applies the healthcare personnel-configured thresholds when evaluating biomarker data and generating alerts for the associated patients.

Server 110 generates alerts that include ICD-10 codes corresponding to detected biomarker patterns and potential health conditions. The ICD-10 coded alerts facilitate clinical documentation by providing standardized diagnostic codes that healthcare personnel 114 incorporates into patient records and billing submissions. Server 110 selects ICD-10 codes based on machine learning classification of biomarker patterns and provides multiple candidate codes when biomarker patterns are consistent with several potential diagnoses. The ICD-10 coded alerts reduce administrative burden on healthcare personnel 114 by automating initial diagnostic code selection based on objective biomarker data.

Server 110 generates AI-annotated clinical summaries that highlight biomarker values triggering alerts and provide explanations for alert classifications. The AI-annotated clinical summaries include narrative descriptions of detected anomalies, comparisons to patient baseline values, and references to clinical guidelines supporting the alert generation. Healthcare personnel 114 accesses the AI-annotated clinical summaries through second user device 112 to rapidly assess patient status and prioritize clinical responses. The AI-annotated clinical summaries include confidence indicators that communicate the statistical certainty of machine learning model outputs to healthcare personnel 114.

In some embodiments, server 110 operates in an Autonomous Mode when healthcare personnel 114 are unreachable through second user device 112 or other communication channels. In Autonomous Mode, server 110 continues monitoring biomarker data with heightened sensitivity by applying lower alert thresholds and increased scrutiny of rate-of-change patterns. Server 110 sends repeat alerts to user 104 through first user device 106 at defined intervals when initial alerts are not acknowledged or when biomarker patterns continue to indicate health concerns. The repeat alerts include escalating urgency indicators and updated biomarker data reflecting changes since the initial alert.

In Autonomous Mode, server 110 advises user 104 of emergency criteria through first user device 106 interface. The emergency criteria include specific biomarker thresholds, symptom combinations, or time-based conditions that indicate a need for immediate medical attention regardless of healthcare personnel 114 availability. Server 110 provides user 104 with instructions for seeking in-person medical care, contacting emergency services, or implementing self-care measures based on the detected biomarker patterns. The emergency criteria advisories include location-specific guidance for accessing medical facilities or emergency resources.

In Autonomous Mode, server 110 may initiate contact with secondary designated clinicians when primary healthcare personnel 114 remain unreachable beyond defined time thresholds. User 104 may configure secondary clinician designations through first user device 106 interface, specifying backup healthcare providers authorized to receive alerts and access biomarker data. Server 110 escalates alerts to secondary designated clinicians according to configurable escalation protocols that define time delays, alert severity thresholds, and communication preferences for each designated clinician.

Server 110 generates structured symptom checklists to be completed by user 104 through first user device 106 in response to detected alerts. The structured symptom checklists include questions about physical symptoms, recent activities, medication adherence, and environmental exposures relevant to the detected biomarker patterns. User 104 completes the symptom checklists through first user device 106 interface, and the responses are transmitted to server 110 for integration with biomarker data analysis. The structured symptom checklists enable server 110 to incorporate subjective symptom information with objective biomarker measurements when generating health assessments.

Server 110 generates differential diagnoses based on combined sensor data from wearable medical monitoring device 102 and user input from completed symptom checklists. The differential diagnoses list potential health conditions consistent with the detected biomarker patterns and reported symptoms, ranked by probability based on machine learning model outputs. Server 110 provides user 104 and healthcare personnel 114 with the differential diagnoses through first user device 106 and second user device 112 respectively, along with recommended diagnostic tests or clinical evaluations that may distinguish between candidate diagnoses.

Server 110 recommends triage actions based on detected biomarker patterns and user-reported symptoms. The triage action recommendations include hydration guidance when biomarker patterns indicate dehydration or electrolyte imbalances. Server 110 may recommend antibiotic administration when biomarker patterns and symptoms are consistent with bacterial infection, subject to healthcare personnel 114 authorization and prescription requirements. The triage action recommendations include emergency signaling instructions when biomarker patterns indicate life-threatening conditions requiring immediate medical intervention.

Server 110 may recommend triggering return protocols in space missions or other medically isolated environments when biomarker patterns indicate health conditions that cannot be adequately managed with available resources. The return protocol recommendations are generated based on mission-specific parameters configured by mission medical officers and account for evacuation feasibility, available medical supplies, and projected health trajectory based on biomarker trends. Server 110 transmits return protocol recommendations to mission control systems and designated medical authorities in addition to user 104 and healthcare personnel 114.

Figure 4:
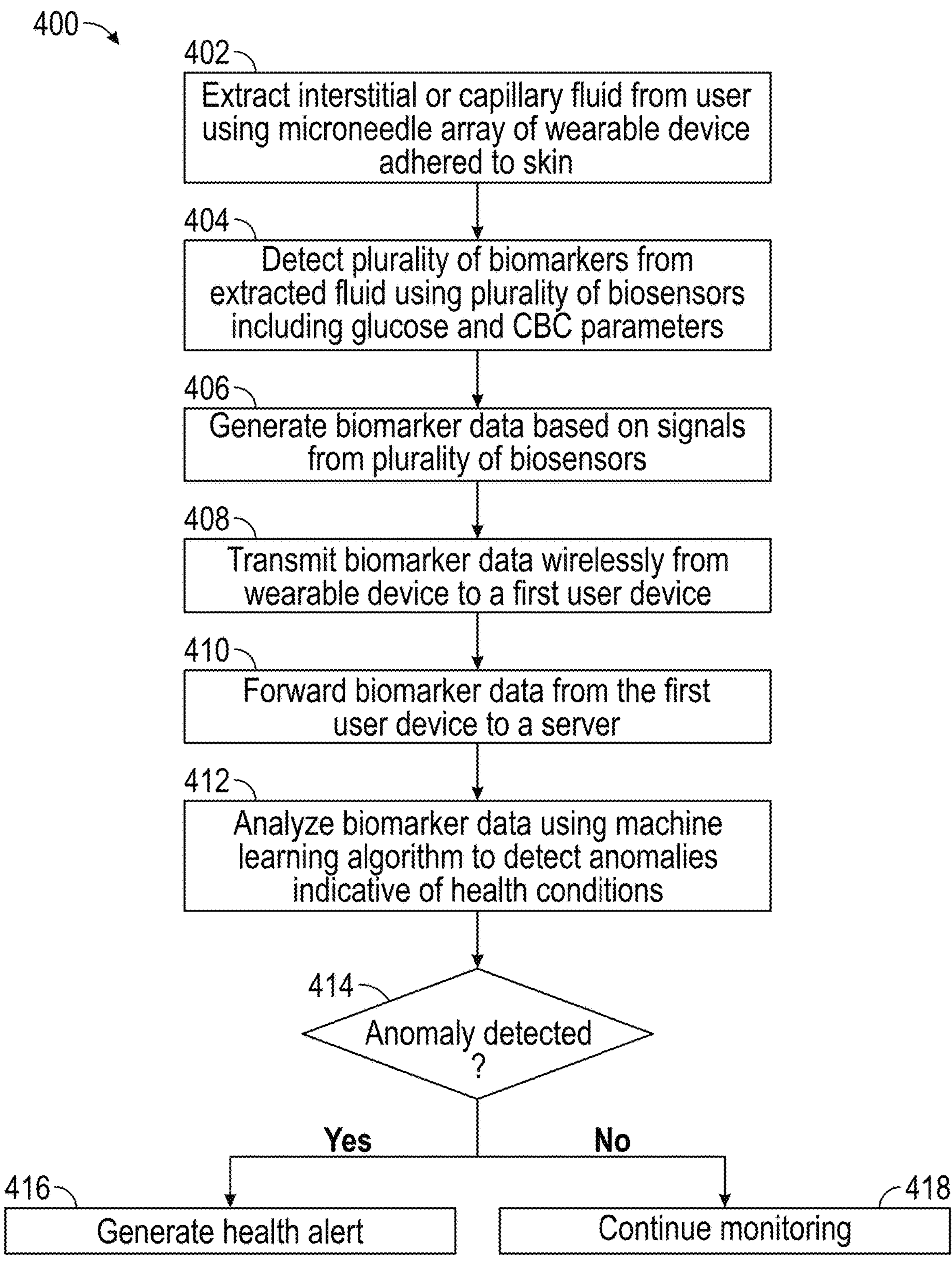
FIG. 4 illustrates a method for continuous health monitoring using a wearable device, in accordance with one embodiment of the present invention.

FIG. 4 shows a method 400 for continuous health monitoring using a wearable device, in accordance with one embodiment of the present invention. The order in which method 400 is described should not be construed as a limitation, and any number of the described process blocks can be combined in any order to implement the process or alternate processes. Additionally, individual blocks may be deleted from method 400 without departing from the spirit and scope of the invention described herein. Furthermore, method 400 can be implemented in any suitable hardware, software, firmware, or combination thereof.

The method 400 starts at step 402. At step 402, the wearable medical monitoring device 102 extracts interstitial or capillary fluid from user 104 using microneedle array 204 adhered to the skin. The microneedle array 204 penetrates through epidermis 302 and dermis 304 of user 104 to access interstitial fluid 306 for biomarker analysis. The fluid extraction at step 402 is performed continuously or at periodic intervals based on configured sampling schedules established through first user device 106. The wearable medical monitoring device 102 utilizes capillary action or low-power micro-pumps to transport the extracted fluid through microfluidic channels toward biosensor 202 chambers.

Consider a scenario where user 104 is a diabetic patient requiring continuous glucose monitoring along with complete blood count surveillance. The wearable medical monitoring device 102 is adhered to the upper arm of user 104, with microneedle array 204 penetrating approximately 500-900 micrometers into layers of skin 300 to access interstitial fluid 306. The microneedle array 204 extracts fluid samples every five minutes to enable near-continuous biomarker tracking. Similarly, for an astronaut operating in a medically isolated environment aboard a spacecraft, the wearable medical monitoring device 102 extracts fluid samples at configurable intervals to monitor for radiation-induced changes in blood cell counts and metabolic parameters.

At step 404, the biosensor 202 detects a plurality of biomarkers from the extracted fluid. The biosensor 202 detects glucose and complete blood count (CBC) parameters including white blood cells (WBC), red blood cells (RBC), hemoglobin, hematocrit, and platelet count. The biosensor 202 additionally detects hemoglobin A1c (HbA1c), prostate-specific antigen (PSA) for male users, and other biochemical indicators based on the sensor configuration of wearable medical monitoring device 102. The biosensor 202 comprises electrochemical sensors for detecting glucose and lactate, aptamer-based sensors for detecting PSA and cytokines, optical biosensors for cell counting and hemoglobin levels, and impedance-based sensors for cell morphology and WBC differentials.

Further, the biosensor 202 detects elevated white blood cell counts in a user 104 who is developing an early-stage infection before clinical symptoms manifest. The biosensor 202 simultaneously detects glucose levels, enabling correlation between metabolic stress responses and immune system activation. For a user 104 working in an industrial setting, the biosensor 202 detects heavy metals such as arsenic, cadmium, cobalt, and mercury in addition to standard CBC parameters, providing occupational health surveillance capabilities.

At step 406, the microprocessor 206 generates biomarker data based on signals from the biosensor 202. The microprocessor 206 receives analog signals from the biosensor 202 and performs signal filtering, amplification, and analog-to-digital conversion to generate digital biomarker data. The microprocessor 206 applies calibration factors and compensation adjustments based on temperature and pH conditions detected during fluid sampling. The biomarker data generated at step 406 includes numerical values representing concentrations or counts for each detected biomarker along with associated timestamps and sensor identification information.

Further, the microprocessor 206 generates biomarker data indicating a glucose concentration of 145 mg/dL, a white blood cell count of 11,500 cells per microliter, and a hemoglobin level of 14.2 g/dL from a single fluid sample extraction. The microprocessor 206 applies temperature compensation to adjust the glucose reading based on a detected skin temperature of 35.8 degrees Celsius. The microprocessor 206 packages the biomarker data with a timestamp indicating the precise moment of sample collection and a unique identifier for the biosensor 202 that performed the detection.

At step 408, the wireless communication module 208 transmits the biomarker data wirelessly from wearable medical monitoring device 102 to first user device 106. The wireless communication module 208 transmits the biomarker data using Bluetooth™ Low Energy (BLE) or other wireless communication protocols such as Zigbee™ or LoRa™. The wireless communication module 208 packages the biomarker data with device identifiers and transmission sequence numbers to enable data integrity verification by first user device 106. The wireless communication module 208 buffers biomarker data within wearable medical monitoring device 102 when first user device 106 is temporarily unavailable and transmits the buffered data when connectivity is re-established.

Consider a scenario where user 104 is exercising and first user device 106 is temporarily out of Bluetooth™ range. The wireless communication module 208 caches biomarker readings collected during the exercise session in onboard memory of wearable medical monitoring device 102. When user 104 returns within range of first user device 106, the wireless communication module 208 automatically synchronizes the cached biomarker data, ensuring no readings are lost during periods of temporary disconnection. For a submariner operating in an environment with restricted wireless communications, the wireless communication module 208 utilizes Near-Field Communication (NFC) protocols to transfer accumulated biomarker data when first user device 106 is brought into close proximity with wearable medical monitoring device 102.

At step 410, the first user device 106 forwards the biomarker data to server 110 through network 108. The first user device 106 packages the biomarker data with timestamps, user metadata, and device diagnostics before transmission. The first user device 106 encrypts the biomarker data using Transport Layer Security (TLS) 1.3 protocols before uploading to server 110. The first user device 106 verifies successful receipt of the biomarker data by server 110 and retransmits data packets that are not acknowledged within defined timeout periods.

The first user device 106 appends user profile information including age, sex, and known medical conditions to the biomarker data packet before transmission to server 110. The first user device 106 includes environmental context data such as current altitude and ambient temperature obtained from device sensors to enable server 110 to apply appropriate calibration adjustments during analysis. For a user 104 traveling to a high-altitude location, the first user device 106 includes altitude data that enables server 110 to adjust hemoglobin and hematocrit thresholds to account for physiological adaptations to reduced oxygen availability.

At step 412, the server 110 analyzes the biomarker data using machine learning algorithms to detect anomalies indicative of health conditions. The server 110 applies time-series forecasting models using Long Short-Term Memory (LSTM) neural networks to detect trends and deviations over time. The LSTM neural networks analyze continuous biomarker data streams to identify rate-of-change patterns and predict future biomarker trajectories based on historical data. The server 110 applies unsupervised anomaly detection algorithms such as isolation forests and k-means clustering for detecting rare patterns not present in training data. The isolation forests identify outlier biomarker readings that deviate from established patterns without requiring labeled training examples. The k-means clustering groups biomarker data points into clusters and flags data points that do not conform to established cluster boundaries as potential anomalies. The server 110 applies classification models such as random forests and logistic regression for risk scoring based on combinations of CBC and metabolic markers. The random forest models evaluate multiple biomarker values simultaneously to generate risk scores for specific health conditions. The logistic regression models calculate probability estimates for binary health outcomes based on weighted combinations of biomarker inputs. The server 110 applies ensemble models that integrate multiple analytical perspectives to improve robustness and reduce false positive rates by requiring agreement across multiple model types before generating alerts.

Server 110 includes confidence scores on predictions and fallback rulesets based on clinical guidelines from the World Health Organization (WHO) and Centers for Disease Control and Prevention (CDC). The confidence scores indicate the reliability of machine learning model outputs based on data quality, model uncertainty, and similarity to training data distributions. When confidence scores fall below defined thresholds, server 110 applies fallback rulesets derived from established clinical guidelines to generate alerts based on absolute biomarker values rather than machine learning predictions. Server 110 includes rate-of-change detectors that trigger alerts even if absolute values remain within normal limits. The rate-of-change detectors monitor the velocity and acceleration of biomarker value changes over time, enabling early warning of rapidly evolving health conditions before biomarker values reach abnormal ranges.

In some embodiments, the unsupervised anomaly detection model comprises isolation forests configured with a plurality of decision trees, wherein each tree is trained on a random subset of biomarker data samples. The isolation forests are configured with parameters including a number of trees ranging from 100 to 500, a sample size for each tree, and a contamination parameter representing the expected proportion of anomalous readings. The isolation forests identify outlier biomarker readings by measuring the average path length required to isolate each data point, wherein shorter path lengths indicate anomalous values that are easier to separate from normal readings. Server 110 applies k-means clustering to group biomarker data points into clusters based on Euclidean distance metrics, wherein the number of clusters is determined through elbow method analysis or silhouette scoring. Data points that fall outside established cluster boundaries or exceed a distance threshold from cluster centroids are flagged as potential anomalies. The unsupervised anomaly detection models are trained on baseline biomarker data collected during the calibration period to establish normal patterns for each user 104, and subsequently applied to incoming biomarker data to detect deviations from established baselines.

In some embodiments, the classification models including random forests and logistic regression are trained using labeled training data comprising biomarker values associated with known health conditions and normal physiological states. The random forest models are configured with parameters including a number of decision trees ranging from 100 to 1000, maximum tree depth, and minimum samples per leaf node. Feature selection for the classification models includes CBC parameters such as white blood cell count, red blood cell count, hemoglobin, hematocrit, and platelet count, along with metabolic markers including glucose and hemoglobin A1c. The classification models generate probability scores ranging from 0 to 1 for specific health conditions including infection risk, anemia risk, and metabolic dysfunction risk. The logistic regression models calculate weighted combinations of biomarker inputs to produce risk scores, wherein the weights are learned during model training on population-level health data. Server 110 applies threshold values to the probability scores to classify risk levels as low, moderate, or high for each health condition category.

In some embodiments, the ensemble models combine outputs from the time-series forecasting model, the unsupervised anomaly detection model, and the classification models using voting mechanisms and weighted averaging. The ensemble models apply majority voting wherein an alert is generated only when a majority of constituent models indicate an anomaly, thereby reducing false positive rates compared to single-model approaches. In some cases, the ensemble models apply weighted averaging wherein outputs from each constituent model are multiplied by confidence weights reflecting model reliability for specific biomarker categories. Agreement across multiple model types is determined by comparing model outputs against configurable agreement thresholds, wherein higher thresholds require stronger consensus before generating alerts. The ensemble approach improves robustness by requiring corroboration from multiple analytical perspectives, reducing the likelihood that noise or artifacts in individual model outputs trigger false alerts.

In some embodiments, the one or more machine learning models are updated via federated learning wherein model training occurs locally on distributed user devices and only model parameter updates are transmitted to server 110 for aggregation. The federated learning implementation comprises local model training on first user device 106 using biomarker data collected from wearable medical monitoring device 102, computation of gradient updates or model parameter changes based on the local training, and transmission of the gradient updates to server 110 without transmitting raw biomarker data. Server 110 aggregates model parameter updates from multiple users using federated averaging, wherein parameter updates from each user are weighted based on the amount of local training data and combined to produce updated global model parameters. The updated global model parameters are periodically distributed back to first user device 106 for application to local model instances. Anonymization of the federated learning process is achieved through differential privacy techniques wherein noise is added to gradient updates before transmission to prevent reconstruction of individual user data from the aggregated updates. The anonymization process further includes k-anonymity measures ensuring that model updates cannot be attributed to fewer than k individual users, and removal of personally identifiable information from all data transmitted during the federated learning process. The federated learning approach enables continuous model improvement using data from thousands of users while maintaining user privacy by ensuring that raw biomarker values never leave user devices.

The server 110 compares current white blood cell counts against personalized baseline values established for user 104 and detecting a statistically significant elevation indicating potential infection onset. The server 110 correlates the elevated WBC count with a concurrent increase in body temperature detected through auxiliary sensors and a slight decrease in glucose stability, generating a multi-factor risk assessment. The server 110 applies rate-of-change detectors to identify that the WBC count has increased by 15% over the past six hours, triggering an alert even though the absolute value remains within population-normal limits.

At step 414, the server 110 determines whether an anomaly is detected based on the machine learning analysis performed at step 412. The server 110 evaluates outputs from multiple machine learning models and applies ensemble voting or weighted averaging to determine whether detected patterns constitute reportable anomalies. The determination at step 414 accounts for alert threshold configurations established by user 104 through first user device 106 or by healthcare personnel 114 through second user device 112. The server 110 applies different sensitivity levels based on biomarker type and clinical significance.

If an anomaly is detected at step 414, method 400 proceeds to step 416. At step 416, the server 110 generates a health alert based on the detected anomaly. The server 110 classifies the detected anomaly by priority level including low priority for non-urgent deviations, moderate priority for significant but non-immediate issues, and high priority for acute changes with potential for rapid deterioration. The server 110 generates AI-annotated clinical summaries, trend visualizations, and suggested actions to accompany the health alert. The server 110 transmits the health alert to user 104 through first user device 106 and transmits alerts to healthcare personnel 114 through second user device 112 when the detected anomaly meets escalation criteria.

The server 110 generates a high priority alert for user 104 indicating a rapid decline in platelet count that may suggest developing thrombocytopenia. The health alert includes a confidence score of 87%, a trend graph showing platelet count decline over the past 48 hours, suggested ICD-10 codes for clinical documentation, and a recommendation for user 104 to seek immediate medical evaluation. The server 110 simultaneously transmits the alert to healthcare personnel 114 through second user device 112, preloading the physician dashboard with the AI-annotated clinical summary and relevant biomarker history.

If no anomaly is detected at step 414, method 400 proceeds to step 418. At step 418, the server 110 continues monitoring without generating alert notifications. The server 110 logs the analyzed biomarker data and updates the dynamic health profile for user 104. The server 110 updates personalized baseline values based on the newly received biomarker data and adjusts machine learning model parameters through federated learning processes. Method 400 returns to step 402 following step 418 to continue the continuous monitoring cycle, with wearable medical monitoring device 102 extracting additional fluid samples for subsequent biomarker detection and analysis by biosensor 202, microprocessor 206, and server 110.

Figure 5:
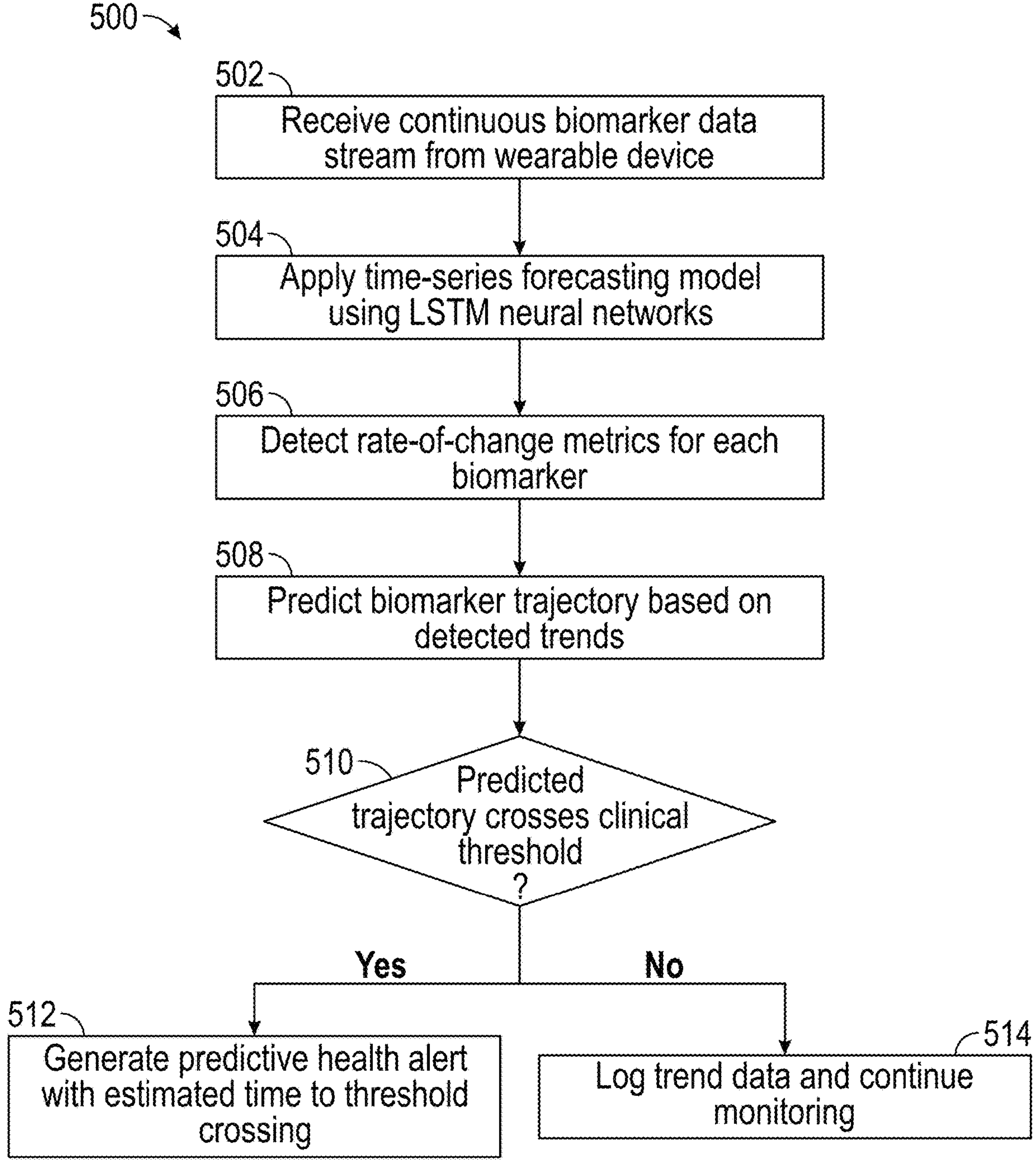
FIG. 5 illustrates a method for time-series forecasting analysis of biomarker data, in accordance with one embodiment of the present invention.

FIG. 5 shows a method 500 for time-series forecasting analysis of biomarker data from wearable medical monitoring device 102, in accordance with one embodiment of the present invention. The order in which method 500 is described should not be construed as a limitation, and any number of the described process blocks can be combined in any order to implement the process or alternate processes. Additionally, individual blocks may be deleted from method 500 without departing from the spirit and scope of the invention described herein. Furthermore, method 500 can be implemented in any suitable hardware, software, firmware, or combination thereof.

Method 500 starts at a step 502. At step 502, server 110 receives a continuous biomarker data stream from wearable medical monitoring device 102 through first user device 106 and network 108. The continuous biomarker data stream includes time-stamped biomarker readings collected by wearable medical monitoring device 102 at configured sampling intervals. The biomarker data stream received at step 502 includes glucose values, complete blood count parameters, hemoglobin A1c measurements, and other biomarkers detected by wearable medical monitoring device 102. Server 110 buffers the incoming biomarker data stream and organizes the data into time-ordered sequences for subsequent time-series analysis.

At a step 504, server 110 applies a time-series forecasting model using Long Short-Term Memory (LSTM) neural networks to the received biomarker data. The LSTM neural networks process sequential biomarker readings to identify temporal patterns and dependencies within the data stream. The time-series forecasting model applied at step 504 analyzes historical biomarker values for user 104 to establish baseline patterns and detect deviations from established trends. The LSTM neural networks maintain internal state representations that capture long-term dependencies in biomarker trajectories, enabling detection of gradual changes that may not be apparent from individual readings.

In some embodiments, the time-series forecasting model comprises a Long Short-Term Memory (LSTM) neural network configured with multiple layers including an input layer, one or more hidden LSTM layers, and an output layer. The LSTM neural network is configured with parameters including a number of hidden units ranging from 32 to 256 per LSTM layer, an input sequence length representing the number of historical biomarker readings provided as input, and an output configuration specifying the prediction horizon for forecasted biomarker values. The LSTM neural network maintains internal state representations comprising a cell state and a hidden state for each LSTM unit, wherein the cell state captures long-term dependencies in biomarker trajectories and the hidden state captures short-term patterns relevant to the current prediction. The LSTM architecture includes forget gates configured to selectively discard information from the cell state, input gates configured to selectively add new information to the cell state, and output gates configured to selectively output information from the cell state to the hidden state. The gate mechanisms enable the LSTM neural network to learn which biomarker patterns are relevant for long-term trajectory prediction and which patterns represent transient fluctuations that should be discarded.

In some embodiments, the rate-of-change metrics detected by the LSTM neural network comprise first derivative calculations representing the velocity of biomarker value changes over time and second derivative calculations representing the acceleration of biomarker value changes. The first derivative is calculated as the difference between consecutive biomarker readings divided by the time interval between readings, providing a measure of how rapidly biomarker values are increasing or decreasing. The second derivative is calculated as the difference between consecutive first derivative values divided by the time interval, providing a measure of whether the rate of change is itself increasing, decreasing, or remaining stable. The LSTM neural network is trained on historical biomarker sequences comprising time-stamped biomarker readings collected from user populations, wherein the training process optimizes network weights to minimize prediction error between forecasted biomarker values and actual observed values. The training data includes biomarker sequences exhibiting various patterns including stable baselines, gradual trends, rapid changes, and cyclical variations corresponding to diurnal rhythms. Trajectory prediction is performed by feeding a current biomarker sequence through the trained LSTM neural network to generate predicted future biomarker values at specified time horizons, wherein the predicted values are compared against clinical thresholds to determine whether alerts should be generated.

With continued reference to FIG. 5, at a step 506, server 110 detects rate-of-change metrics for each biomarker in the data stream. The rate-of-change metrics include velocity measurements indicating how rapidly biomarker values are increasing or decreasing over time. Server 110 calculates acceleration metrics indicating whether the rate of change is itself increasing, decreasing, or remaining stable. The rate-of-change metrics detected at step 506 enable server 110 to identify biomarker trends that indicate emerging health conditions before absolute values cross clinical thresholds.

Consider a scenario where server 110 detects that hemoglobin levels for user 104 are decreasing at a rate of 0.2 g/dL per day based on the rate-of-change metrics calculated at step 506. The server 110 identifies this declining trend even though current hemoglobin values remain within normal population reference ranges. For a user 104 experiencing early-stage internal bleeding, the rate-of-change detection at step 506 enables identification of the condition before hemoglobin values fall to clinically anemic levels.

At a step 508, server 110 predicts biomarker trajectory based on the detected trends and rate-of-change metrics. The trajectory prediction at step 508 extrapolates current biomarker trends forward in time to estimate future biomarker values. Server 110 applies the LSTM time-series forecasting model to generate probability distributions for predicted future biomarker values at specified time horizons. The trajectory prediction accounts for historical patterns in biomarker behavior for user 104, including diurnal variations, responses to activities, and medication effects.

Server 110 predicts that hemoglobin levels for user 104 will cross the clinical anemia threshold of 12.0 g/dL within five days based on the current rate of hemoglobin decrease. Server 110 generates confidence intervals around the predicted trajectory, indicating that the threshold crossing may occur between four and seven days with 95% probability. The trajectory prediction at step 508 enables proactive clinical intervention before user 104 experiences symptoms associated with anemia.

As further shown in FIG. 5, at a step 510, server 110 determines whether the predicted trajectory crosses a clinical threshold. The clinical thresholds evaluated at step 510 include population-based reference ranges, personalized thresholds established for user 104, and thresholds configured by healthcare personnel 114 through second user device 112. Server 110 evaluates predicted trajectories against multiple threshold types and time horizons to identify potential threshold crossings at various future time points. The determination at step 510 accounts for confidence intervals around predicted trajectories, flagging potential threshold crossings when probability exceeds configured sensitivity levels.

If the predicted trajectory crosses a clinical threshold at step 510, method 500 proceeds to a step 512. At step 512, server 110 generates a predictive health alert with an estimated time to threshold crossing. The predictive health alert generated at step 512 includes the current biomarker value, the predicted trajectory, the clinical threshold that will be crossed, and the estimated time until the crossing occurs. Server 110 transmits the predictive health alert to user 104 through first user device 106 and transmits the alert to healthcare personnel 114 through second user device 112 based on configured escalation protocols.

Server 110 generates a predictive alert stating that hemoglobin is decreasing at 0.2 g/dL per day and that user 104 will cross the clinical anemia threshold in five days at the current rate. The predictive health alert includes a trend graph showing historical hemoglobin values, the detected rate of decline, and the projected trajectory toward the threshold. Server 110 includes recommendations for dietary modifications, iron supplementation, or clinical evaluation based on the predicted trajectory and estimated time to threshold crossing.

If the predicted trajectory does not cross a clinical threshold at step 510, method 500 proceeds to a step 514. At step 514, server 110 logs trend data and continues monitoring without generating alert notifications. Server 110 stores the calculated rate-of-change metrics and trajectory predictions in the dynamic health profile for user 104. The logged trend data is used to refine future trajectory predictions and to establish baseline rate-of-change patterns for user 104. Method 500 returns to step 502 following step 514 to continue receiving and analyzing the continuous biomarker data stream from wearable medical monitoring device 102.

With continued reference to FIG. 5, server 110 performs multi-variable pattern detection to identify complex combinations of biomarker changes associated with specific health risks. Server 110 analyzes correlations between multiple biomarkers in the continuous data stream to detect patterns that individual biomarker analysis may not identify. The multi-variable pattern detection applies machine learning models trained on combinations of biomarker values and their temporal relationships.

Server 110 detects a combination of rising white blood cell count, increasing temperature, and falling hematocrit that suggests sepsis in user 104. The multi-variable pattern detection identifies this combination even when individual biomarker values remain within normal ranges, as the concurrent directional changes across multiple parameters indicate systemic infection. Server 110 generates alerts based on detected multi-variable patterns and includes explanations of the biomarker combinations that triggered the pattern detection in alerts transmitted to user 104 through first user device 106 and to healthcare personnel 114 through second user device 112.

Server 110 detects additional multi-variable patterns including falling platelet count combined with high hemoglobin concentration suggesting dehydration with hemoconcentration, and subtle white blood cell elevation with normal glucose but rising cortisol indicating early stress response or immune suppression. The multi-variable pattern detection capabilities of server 110 enable identification of health conditions that manifest through coordinated changes across multiple physiological systems rather than through isolated biomarker abnormalities. Server 110 applies the multi-variable pattern detection in conjunction with the time-series forecasting analysis of method 500 to provide comprehensive health surveillance for user 104.

Figure 6:
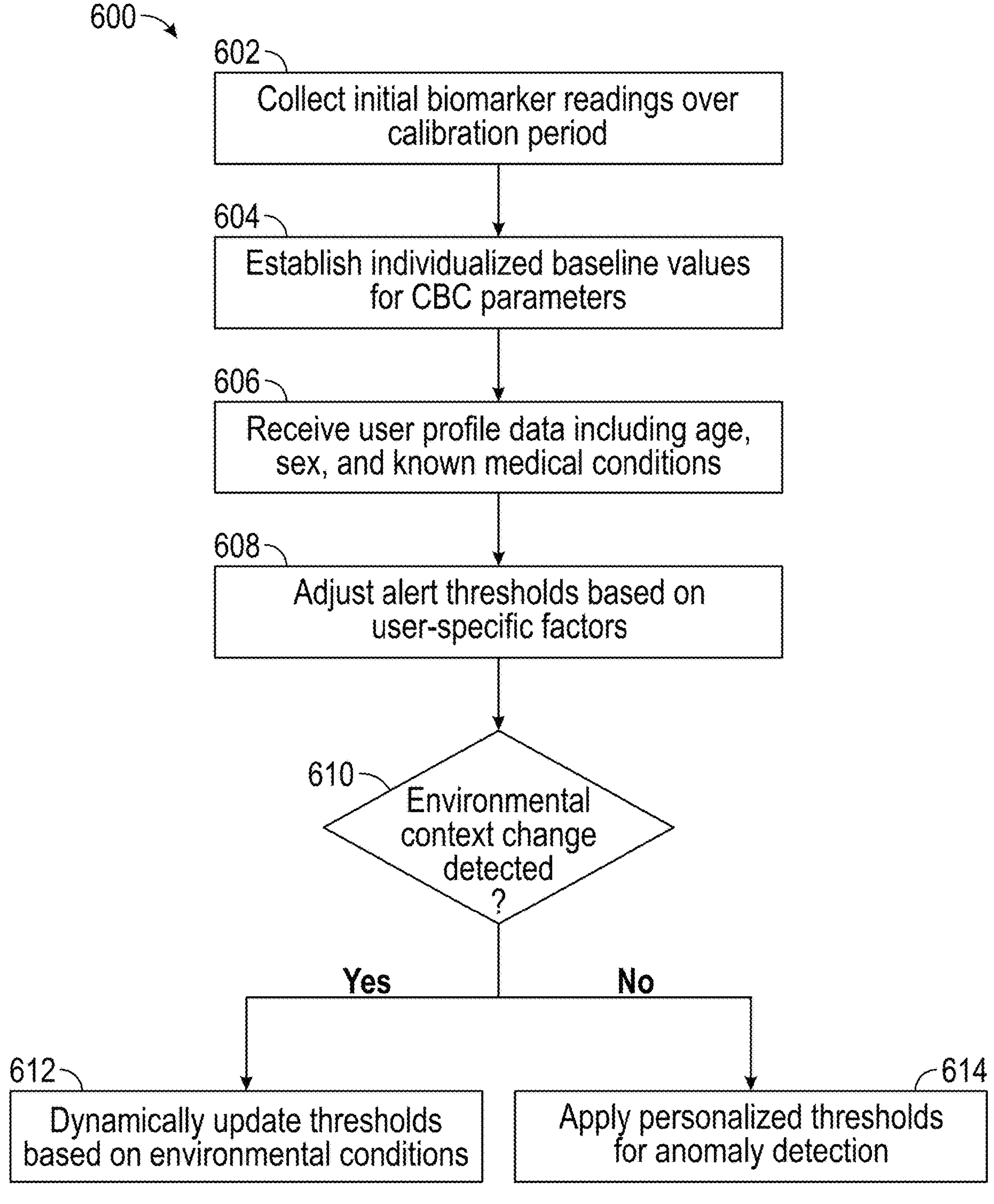
FIG. 6 illustrates a method for personalized baseline establishment, in accordance with one embodiment of the present invention.

FIG. 6 shows a method 600 for personalized baseline establishment, in accordance with one embodiment of the present invention. The order in which method 600 is described should not be construed as a limitation, and any number of the described process blocks can be combined in any order to implement the process or alternate processes. Additionally, individual blocks may be deleted from method 600 without departing from the spirit and scope of the invention described herein. Furthermore, method 600 can be implemented in any suitable hardware, software, firmware, or combination thereof.

Method 600 starts at a step 602. At step 602, server 110 collects initial biomarker readings over a calibration period from wearable medical monitoring device 102. The calibration period spans multiple days or weeks during which wearable medical monitoring device 102 continuously or periodically samples biomarkers from user 104 and transmits the biomarker data to server 110 through first user device 106 and network 108. Server 110 accumulates biomarker readings during the calibration period to establish a statistically representative sample of biomarker values for user 104 under various physiological states and daily activity patterns. The calibration period at step 602 captures diurnal variations in biomarker values, responses to meals and physical activity, and natural fluctuations in blood chemistry that occur in user 104 during normal daily routines.

Server 110 builds a dynamic health profile for each user 104 that establishes individualized baselines for CBC parameters and adjusts alert thresholds based on age, sex, known conditions, and environmental context. The dynamic health profile stores historical biomarker values for user 104 and calculates personalized reference ranges that account for individual physiological variations. Server 110 updates the dynamic health profile as new biomarker data is received, allowing the individualized baselines to adapt to changes in user 104 health status over time.

Server 110 performs dynamic calibration based on time-of-day physiological fluctuations, environmental conditions such as temperature and altitude, and user-specific baseline values over time. The dynamic calibration adjusts biomarker interpretation thresholds to account for circadian variations in blood chemistry and metabolic markers. Server 110 receives environmental context data from first user device 106 or external data sources and applies correction factors to biomarker readings based on detected environmental conditions. The dynamic calibration reduces false alerts caused by normal physiological variations unrelated to health conditions.

Consider a scenario where user 104 is a newly enrolled patient beginning continuous health monitoring with wearable medical monitoring device 102. During the calibration period at step 602, server 110 collects glucose readings, complete blood count parameters, and other biomarker values at five-minute intervals over a fourteen-day period. Server 110 records biomarker values during various activities including sleep, exercise, meals, and work periods to capture the full range of physiological states experienced by user 104. The calibration period enables server 110 to distinguish between normal biomarker variations for user 104 and abnormal deviations that may indicate health conditions.

At a step 604, server 110 establishes individualized baseline values for complete blood count (CBC) parameters based on the biomarker readings collected during the calibration period at step 602. Server 110 calculates statistical measures including mean values, standard deviations, and percentile distributions for each CBC parameter including white blood cells, red blood cells, hemoglobin, hematocrit, and platelet count. The individualized baseline values established at step 604 account for natural physiological variations specific to user 104 that may differ from population-based reference ranges. Server 110 establishes separate baseline values for different times of day, activity states, or other contextual factors identified during the calibration period.

Server 110 establishes that user 104 has a baseline hemoglobin level of 15.2 g/dL with a standard deviation of 0.4 g/dL, which differs from the population mean of 14.0 g/dL for individuals of similar age and sex. Server 110 establishes that white blood cell counts for user 104 typically range between 5,500 and 7,200 cells per microliter during resting states and increase to 8,000-9,500 cells per microliter following vigorous exercise. The individualized baseline values established at step 604 enable server 110 to detect deviations from normal patterns for user 104 that would not be flagged using population-based reference ranges.

With continued reference to FIG. 6, at a step 606, server 110 receives user profile data including age, sex, and known medical conditions for user 104. The user profile data is entered by user 104 through first user device 106 during initial system configuration or is imported from electronic health records through integration with healthcare provider systems. Server 110 receives user profile data including demographic information, medical history, current medications, allergies, and chronic conditions that may affect biomarker interpretation. The user profile data received at step 606 is stored in the dynamic health profile maintained by server 110 for user 104.

Server 110 receives user profile data indicating that user 104 is a 62-year-old male with a history of type 2 diabetes and hypertension, currently taking metformin and lisinopril. Server 110 receives information that user 104 has a known iron deficiency that has been previously treated with supplementation. The user profile data received at step 606 enables server 110 to interpret biomarker values in the context of known medical conditions and medication effects that may influence normal biomarker ranges for user 104.

At a step 608, server 110 adjusts alert thresholds based on user-specific factors derived from the user profile data received at step 606 and the individualized baseline values established at step 604. Server 110 modifies default alert thresholds for specific biomarkers based on age-related physiological changes, sex-specific reference ranges, and known medical conditions that affect normal biomarker values. The adjusted alert thresholds at step 608 account for medication effects that may alter biomarker levels without indicating pathological conditions. Server 110 applies machine learning models trained on user populations with similar demographic and medical profiles to optimize threshold adjustments for user 104.

Server 110 adjusts the glucose alert threshold for user 104 to account for the type 2 diabetes diagnosis and metformin treatment, setting a higher upper threshold that reflects therapeutic glucose targets rather than population-normal ranges. Server 110 adjusts hemoglobin alert thresholds to account for the known iron deficiency history, applying lower sensitivity to mild hemoglobin decreases while maintaining high sensitivity to rapid declines that may indicate acute blood loss. The threshold adjustments at step 608 reduce false positive alerts caused by known medical conditions while preserving sensitivity to new or worsening health conditions.

As further shown in FIG. 6, at a step 610, server 110 determines whether an environmental context change has been detected. Server 110 receives environmental context data from first user device 106 including current altitude, ambient temperature, humidity, and geographic location. The environmental context data is obtained from sensors integrated in first user device 106 or from external data sources accessed through network 108. Server 110 compares current environmental conditions against baseline environmental conditions established during the calibration period to detect changes that may affect biomarker interpretation.

Further, server 110 detects user 104 traveling from a sea-level location to a high-altitude destination at 2,500 meters elevation based on altitude data received from first user device 106. Server 110 detects environmental context changes including temperature extremes, changes in time zone that may affect circadian biomarker patterns, or travel to geographic regions with different atmospheric conditions. The environmental context change detection at step 610 enables server 110 to anticipate physiological adaptations that may affect biomarker values independently of health conditions.

If an environmental context change is detected at step 610, method 600 proceeds to a step 612. At step 612, server 110 dynamically updates alert thresholds based on the detected environmental conditions. Server 110 applies altitude-specific adjustments to hemoglobin and hematocrit thresholds to account for physiological adaptations to reduced oxygen availability at high elevations. The dynamic threshold updates at step 612 account for temperature-related effects on blood viscosity and metabolic rate that may influence biomarker values. Server 110 applies time-based threshold adjustments when time zone changes are detected to account for circadian variations in biomarker levels.

Server 110 increases the upper threshold for hemoglobin and hematocrit values by 8% to account for the physiological response to high-altitude conditions detected at step 610. Server 110 applies a gradual threshold adjustment over several days to account for the progressive nature of altitude acclimatization. The dynamic threshold updates at step 612 prevent false positive alerts that would otherwise be generated as user 104 undergoes normal physiological adaptation to the changed environmental conditions.

If no environmental context change is detected at step 610, or following the dynamic threshold updates at step 612, method 600 proceeds to a step 614. At step 614, server 110 applies the personalized thresholds for anomaly detection during ongoing biomarker monitoring. The personalized thresholds applied at step 614 include the individualized baseline values established at step 604, the user-specific adjustments made at step 608, and any dynamic environmental adjustments made at step 612. Server 110 compares incoming biomarker data from wearable medical monitoring device 102 against the personalized thresholds to detect anomalies that represent deviations from normal patterns for user 104.

Server 110 applies the personalized hemoglobin threshold of 14.0 g/dL for user 104, which is lower than the population-based threshold of 12.0 g/dl due to the established baseline of 15.2 g/dL for user 104. Server 110 detects a hemoglobin reading of 13.8 g/dL as a potential anomaly warranting attention, even though this value would be considered normal using population-based reference ranges. The personalized threshold application at step 614 enables detection of health conditions at earlier stages when biomarker changes are still within population-normal ranges but represent deviations from individual baseline patterns.

With continued reference to FIG. 6, method 600 operates as a continuous process with server 110 periodically re-evaluating environmental context at step 610 and updating thresholds as conditions change. Server 110 refines the individualized baseline values established at step 604 over time as additional biomarker data is collected from wearable medical monitoring device 102. The personalized baseline establishment process of method 600 enables server 110 to provide increasingly accurate anomaly detection as the dynamic health profile for user 104 becomes more comprehensive through extended monitoring periods.

Server 110 receives updated user profile data at step 606 when healthcare personnel 114 enters new medical diagnoses, medication changes, or other clinical information through second user device 112. The updated user profile data triggers re-execution of step 608 to adjust alert thresholds based on the new clinical information. Method 600 thereby maintains current and accurate personalized thresholds that reflect the evolving health status and medical management of user 104.

Figure 7:
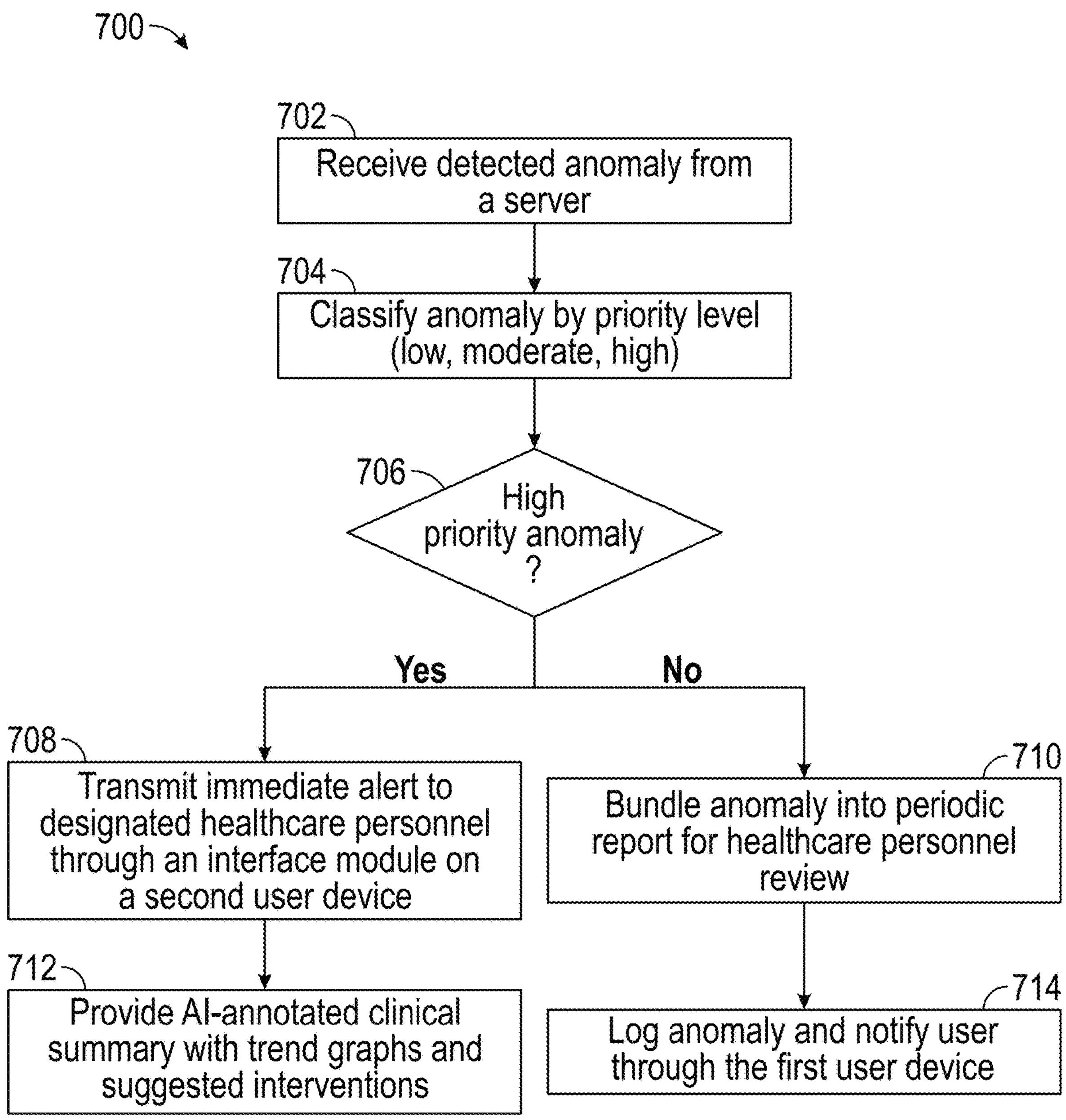
FIG. 7 illustrates a method for healthcare provider alert transmission, in accordance with one embodiment of the present invention.

FIG. 7 shows a method 700 for healthcare provider alert transmission, in accordance with one embodiment of the present invention. The order in which method 700 is described should not be construed as a limitation, and any number of the described process blocks can be combined in any order to implement the process or alternate processes. Additionally, individual blocks may be deleted from method 700 without departing from the spirit and scope of the invention described herein. Furthermore, method 700 can be implemented in any suitable hardware, software, firmware, or combination thereof.

Method 700 starts at a step 702. At step 702, the server 110 receives a detected anomaly from machine learning analysis of biomarker data collected by the wearable medical monitoring device 102. The detected anomaly received at step 702 includes biomarker values that deviate from personalized baseline thresholds established for the user 104, rate-of-change patterns indicating potential health deterioration, or multi-variable combinations suggesting specific health conditions. The server 110 receives the detected anomaly as output from time-series forecasting models, unsupervised anomaly detection algorithms, classification models, or ensemble models that analyze biomarker data streams transmitted from the wearable medical monitoring device 102 through the first user device 106 and the network 108.

Consider a scenario where the server 110 receives a detected anomaly indicating that white blood cell counts for the user 104 have increased by 35% over a 12-hour period while hemoglobin levels have concurrently decreased by 0.8 g/dL. The detected anomaly received at step 702 includes confidence scores from the machine learning models, the specific biomarker values triggering the detection, timestamps indicating when the anomalous readings occurred, and references to the baseline values against which the anomaly was identified. The server 110 receives detected anomalies from multiple concurrent analysis processes and queues the anomalies for priority classification at subsequent steps of method 700.

At a step 704, the server 110 classifies the detected anomaly by priority level. The priority classification at step 704 assigns the detected anomaly to one of three escalation levels: low priority for non-urgent deviations that may be logged silently or bundled into periodic reports, moderate priority for significant but non-immediate issues that may be forwarded with suggested next steps, and high priority for acute changes with potential for rapid deterioration that trigger immediate provider alerts and patient notifications. The server 110 applies classification criteria based on the magnitude of biomarker deviations, the rate of change in biomarker values, the clinical significance of affected biomarkers, and the confidence scores from machine learning model outputs.

Server 110 classifies the detected anomaly involving concurrent white blood cell elevation and hemoglobin decline as high priority based on the multi-variable pattern suggesting potential sepsis or acute infection with blood loss. The server 110 applies classification rules that elevate priority levels when multiple biomarkers exhibit concurrent abnormal trends, when rate-of-change metrics exceed defined thresholds, or when detected patterns match profiles associated with time-sensitive health conditions. The priority classification at step 704 accounts for user-specific factors including known medical conditions, current medications, and healthcare personnel-configured sensitivity settings accessed through the second user device 112.

With continued reference to FIG. 7, at a step 706, the server 110 determines whether the detected anomaly is classified as high priority based on the classification performed at step 704. The determination at step 706 evaluates the assigned priority level against escalation criteria that define which anomalies require immediate healthcare personnel notification versus those that may be handled through periodic reporting or user notification alone. The server 110 applies configurable escalation rules that healthcare personnel 114 establishes through the second user device 112 to customize the threshold between high priority and lower priority classifications for specific patients or biomarker categories.

If the detected anomaly is determined to be high priority at step 706, method 700 proceeds to a step 708. At step 708, the server 110 transmits an immediate alert to designated healthcare personnel 114 through an interface module on the second user device 112. The immediate alert transmitted at step 708 includes the detected biomarker values, the priority classification, timestamps indicating when the anomaly was detected, and preliminary clinical context derived from the machine learning analysis. The server 110 transmits the immediate alert through multiple communication channels including push notifications, email, SMS messages, or direct integration with clinical communication systems to ensure timely delivery to healthcare personnel 114.

Server 110 transmits an immediate alert to healthcare personnel 114 indicating that the user 104 exhibits biomarker patterns consistent with developing sepsis, with white blood cell count elevated to 14,200 cells per microliter and hemoglobin declining at 0.4 g/dL per six hours. The immediate alert transmitted at step 708 includes urgency indicators, recommended response timeframes, and contact information for the user 104 to facilitate rapid clinical follow-up. The server 110 logs the transmission of the immediate alert and initiates escalation protocols if acknowledgment is not received from healthcare personnel 114 within defined time periods.

Following step 708, method 700 proceeds to a step 712. At step 712, the server 110 provides an AI-annotated clinical summary along with trend graphs and suggested interventions to healthcare personnel 114 through the second user device 112. The AI-annotated clinical summary provided at step 712 includes narrative descriptions of the detected anomaly, explanations of which biomarker values and patterns contributed to the alert classification, and references to clinical guidelines supporting the analysis. The trend graphs display time-series visualizations of the affected biomarkers over configurable time periods, showing the trajectory of values leading to the detected anomaly.

Server 110 provides a clinical summary stating that white blood cell counts have risen from a baseline of 6,800 cells per microliter to 14,200 cells per microliter over 18 hours while hemoglobin has declined from 14.8 g/dl to 13.2 g/dL, with the combination suggesting systemic inflammatory response with possible hemorrhage. The suggested interventions provided at step 712 include recommendations for blood cultures, complete metabolic panel, imaging studies, or empiric antibiotic therapy based on the detected biomarker patterns. The server 110 includes suggested ICD-10 codes corresponding to the detected patterns to facilitate clinical documentation by healthcare personnel 114.

With continued reference to FIG. 7, if the detected anomaly is not determined to be high priority at step 706, method 700 proceeds to a step 710. At step 710, the server 110 bundles the non-high priority anomaly into a periodic report for healthcare personnel 114 review. The periodic report generated at step 710 aggregates multiple low and moderate priority anomalies detected over a defined reporting period such as daily or weekly intervals. The server 110 organizes the bundled anomalies by biomarker category, priority level, or chronological order to facilitate efficient review by healthcare personnel 114 through the second user device 112.

Server 110 bundles a moderate priority anomaly indicating gradual hemoglobin decline of 0.3 g/dL over one week into a weekly summary report for healthcare personnel 114. The periodic report includes trend summaries for each bundled anomaly, suggested follow-up actions, and priority rankings to guide healthcare personnel 114 attention toward the most clinically relevant findings. The server 110 transmits the periodic report to healthcare personnel 114 through the second user device 112 at scheduled intervals or upon request through the physician dashboard interface.

Following step 710, method 700 proceeds to a step 714. At step 714, the server 110 logs the detected anomaly and notifies the user 104 through the first user device 106. The anomaly logging at step 714 records the detected biomarker values, the assigned priority classification, timestamps, and any actions taken in response to the anomaly in the dynamic health profile maintained by the server 110 for the user 104. The user notification transmitted at step 714 includes informational or cautionary alerts appropriate to the priority level of the detected anomaly, along with contextual explanations and suggested actions that the user 104 may take.

Server 110 logs the moderate priority hemoglobin decline anomaly in the health record for the user 104 and transmitting a cautionary alert through the first user device 106 recommending increased iron intake and hydration. The user notification at step 714 includes educational content explaining the significance of the detected biomarker trend and guidance on symptoms that would warrant seeking immediate medical attention. The server 110 updates the dynamic health profile for the user 104 with the logged anomaly information to inform future baseline calculations and anomaly detection processes.

With continued reference to FIG. 7, method 700 operates continuously as the server 110 receives detected anomalies from ongoing biomarker monitoring performed by the wearable medical monitoring device 102. The server 110 processes multiple detected anomalies concurrently, applying the priority classification at step 704 and routing each anomaly through the appropriate pathway based on the determination at step 706. Method 700 thereby enables differentiated handling of health alerts based on clinical urgency, ensuring that high priority conditions receive immediate healthcare personnel attention while lower priority findings are communicated through appropriate channels without generating excessive alert burden.

Server 110 tracks acknowledgment status for immediate alerts transmitted at step 708 and initiates secondary escalation procedures when healthcare personnel 114 do not acknowledge high priority alerts within defined time thresholds. The secondary escalation procedures include retransmission of alerts through alternative communication channels, notification of backup healthcare personnel designated by the user 104, or activation of autonomous mode protocols that provide the user 104 with emergency guidance through the first user device 106. Method 700 thereby ensures that high priority health conditions receive appropriate clinical attention even when primary healthcare personnel 114 are temporarily unavailable.

The health monitoring system described herein provides advantages over prior art systems that monitor single biomarkers or limited sets of physiological parameters. Prior art continuous glucose monitors and similar wearable devices typically focus on tracking a single metabolic indicator, such as glucose concentration, without providing visibility into broader physiological status. The present system enables multi-analyte detection capabilities that detect over sixty biomarkers including complete blood count parameters, metabolic markers, heavy metals, and disease-specific indicators such as prostate-specific antigen. The multi-analyte detection approach provides a comprehensive view of physiological status that single-biomarker devices cannot achieve, enabling detection of health conditions that manifest through changes in multiple biomarker categories simultaneously.

Prior art wearable monitoring devices typically present raw or minimally processed data to users without sophisticated analytical capabilities for pattern recognition or predictive health assessment. The present system incorporates AI-based analysis capabilities including anomaly detection using unsupervised machine learning algorithms, predictive modeling using classification models for risk scoring, and time-series forecasting using Long Short-Term Memory neural networks to detect trends and predict biomarker trajectories. The time-series forecasting capabilities enable detection of rate-of-change patterns and prediction of when biomarker values may cross clinical thresholds, providing advance warning of potential health conditions before symptoms manifest. The anomaly detection capabilities identify rare biomarker patterns not present in training data through isolation forests and k-means clustering, enabling detection of novel health conditions that rule-based systems may not recognize.

Prior art monitoring systems typically lack seamless integration with clinical workflows, requiring manual data export, platform-specific portals, or third-party software to share health information with healthcare providers. The present system supports integration with health systems through Fast Healthcare Interoperability Resources (FHIR) and Health Level Seven (HL7) standards, allowing direct embedding of biomarker data into Electronic Health Records (EHRs). The healthcare provider integration enables automatic forwarding of alerts, trend summaries, and AI-annotated clinical reports to designated healthcare personnel through secure interfaces. The integration capabilities reduce delays between anomaly detection and clinical evaluation by enabling push-based alerting of clinicians with biomarker-level analysis that prior art systems do not support.

The present system performs population-level surveillance by aggregating anonymized biometric trends from multiple users, detecting cohort-wide anomalies in complete blood count or metabolic data, flagging clusters of physiological changes suggestive of contagion or shared environmental stress, and triggering early outbreak detection mechanisms. The population-level surveillance capabilities enable identification of emerging health threats across user populations before individual users exhibit clinical symptoms. When multiple users within a defined population exhibit concurrent biomarker changes such as simultaneous mild white blood cell elevation, the system detects the cohort-wide pattern and generates alerts indicating potential infectious disease transmission or shared environmental exposure.

The present system performs syndromic surveillance by monitoring health indicators in real-time to detect unusual patterns that may signal an outbreak or mass exposure. The syndromic surveillance capabilities track fever-related biomarkers including white blood cell and neutrophil counts, dehydration markers including hematocrit and sodium levels, and other physiological indicators across user populations. The real-time monitoring approach enables detection of outbreak signatures before confirmed diagnoses are available, supporting early public health response to emerging health threats.

The present system integrates complete blood count data with contextual metadata such as air quality measurements, water quality indicators, and carbon dioxide levels to provide real-time correlation matrices between environmental and biological variables. The environmental correlation analysis enables identification of relationships between environmental exposures and physiological responses across user populations. The integration of environmental metadata with biomarker data supports detection of environmental hazards including toxic exposures, radiation events, or atmospheric contamination through correlation with observed biomarker changes. The environmental correlation capabilities are applicable to occupational health surveillance, environmental monitoring in isolated environments such as spacecraft or submarines, and public health assessment of environmental health impacts.

The wearable medical monitoring device is deployed across a range of use cases spanning medically isolated environments, chronic disease management, athletic performance optimization, and healthcare access expansion for underserved populations. The continuous multi-biomarker monitoring capabilities and AI-based analysis features provide health surveillance functionality adapted to the specific requirements of each use case environment.

In some embodiments, astronauts on long-duration space missions may utilize the wearable medical monitoring device to monitor for physiological changes associated with spaceflight including space anemia, radiation exposure effects, and immune dysregulation. The wearable medical monitoring device may detect declining hemoglobin trends and generate predictive alerts indicating when values may cross clinical anemia thresholds. Radiation exposure from galactic cosmic rays and solar particle events may cause hematologic changes detectable through continuous monitoring of white blood cell counts and platelet levels. The wearable medical monitoring device may detect sudden drops in platelet count or white blood cell count that may indicate acute radiation exposure, triggering alerts that enable mission medical officers to assess radiation dose and implement protective measures. Immune dysregulation associated with spaceflight may manifest through changes in white blood cell differential counts and inflammatory markers detectable by the biosensor.

In some embodiments, the wearable medical monitoring device may be suitable for use in extreme physical conditions such as those encountered during extravehicular activity (EVA). The wearable medical monitoring device may continue biomarker sampling and data transmission during EVA operations, providing real-time health surveillance when astronauts are outside spacecraft. The compact form factor and skin-adhered configuration of the wearable medical monitoring device may enable wear beneath EVA suit garments without interfering with suit fit or mobility.

In some embodiments, submariners in isolated naval operations may utilize the wearable medical monitoring device for infection control monitoring and detection of hypercapnia-related physiological changes. The wearable medical monitoring device may detect early signs of infection through continuous monitoring of white blood cell counts, enabling identification of febrile neutrophilia or leukocytosis before clinical symptoms manifest. The wearable medical monitoring device may detect metabolic changes associated with hypercapnia through monitoring of complete blood count parameters and metabolic indicators, enabling correlation of crew health status with atmospheric conditions.

In some embodiments, the wearable medical monitoring device may be suitable for use during high-G submarine maneuvers that subject crew members to acceleration forces affecting cardiovascular function and blood distribution. The continuous monitoring capabilities may detect hematocrit and hemoglobin changes associated with fluid shifts during high-G maneuvers.

In some embodiments, elderly patients may utilize the wearable medical monitoring device for continuous passive monitoring that supports aging in place while maintaining health surveillance. The wearable medical monitoring device may provide continuous monitoring without requiring active user interaction, detecting early signs of urinary tract infection or pneumonia through white blood cell count changes before symptoms escalate. The wearable medical monitoring device may detect hematologic markers of anemia or dehydration that may contribute to fall risk in elderly patients. Automatic alert transmission to adult children, home health providers, or healthcare personnel may enable caregiver notification of concerning biomarker trends.

In some embodiments, athletes and military personnel may utilize the wearable medical monitoring device for human performance optimization through granular biometric monitoring. The wearable medical monitoring device may detect overtraining through monitoring of white blood cell dynamics and stress hormone indicators. Hydration status may be tracked through hematocrit and electrolyte monitoring. Recovery optimization may be supported through monitoring of platelet counts and inflammation markers following injury or intense physical exertion. Altitude and travel adjustment may be monitored through complete blood count adaptation tracking.

In some embodiments, the wearable medical monitoring device may be suitable for use in desert operations and other extreme environmental conditions encountered by military personnel. The wearable medical monitoring device may detect dehydration through hematocrit changes and electrolyte monitoring. The waterproof and sweat-resistant design may maintain device function during elevated perspiration rates associated with desert heat exposure.

In some embodiments, rural and underserved populations with limited access to healthcare facilities may utilize the wearable medical monitoring device to obtain continuous health monitoring. The wearable medical monitoring device may provide point-of-need complete blood count and glucose tracking without requiring access to laboratory facilities. Connection to remote clinicians through smartphone data uploads via the first user device may enable clinical consultation and guidance based on objective biomarker data. The wearable medical monitoring device may support mobile clinic operations and community health worker networks by providing objective biomarker data that informs case management and referral decisions. It should be understood that the foregoing use cases are exemplary, and other applications not explicitly described herein may fall within the scope of the present invention.

In various embodiments, the software components described herein are implemented on one or more general-purpose computers, specialized medical devices, cloud-based servers, mobile computing devices, or distributed computing systems. The methods and systems disclosed are embodied in computer-readable instructions stored on non-transitory computer-readable media, including but not limited to solid-state memory, magnetic storage, optical storage, or combinations thereof. The machine learning algorithms and artificial intelligence models described herein are executed on processors including central processing units (CPUs), graphics processing units (GPUs), application-specific integrated circuits (ASICs), field-programmable gate arrays (FPGAs), or neural processing units configured for inference operations.

In some aspects, the health monitoring system is configured to comply with applicable regulatory requirements for medical devices, including data privacy and security standards for protected health information. The system implements encryption protocols for data transmission between the wearable medical monitoring device, user devices, and servers. In some cases, the system incorporates authentication mechanisms to verify the identity of users and healthcare personnel accessing biomarker data and health alerts.

The biomarker data processing and anomaly detection methods described herein are performed locally on the wearable device, on a user device, on a remote server, or through a combination of local and remote processing. In some embodiments, the distribution of processing tasks is dynamically adjusted based on available computational resources, network connectivity, power constraints, or latency requirements for time-sensitive health alerts.

The machine learning models described herein, including those for anomaly detection and time-series forecasting, are trained using supervised learning, unsupervised learning, reinforcement learning, or combinations thereof. In some aspects, the models are pre-trained on population-level biomarker data and subsequently fine-tuned using individual user data to establish personalized baselines and thresholds. The training data includes labeled examples of normal physiological states and various health conditions to enable classification of detected anomalies.

In some cases, the system is configured to operate in accordance with interoperability standards for health information exchange, enabling integration with electronic health record systems, clinical decision support tools, and healthcare provider communication platforms. The alert transmission mechanisms support multiple communication protocols and are configured to route notifications based on the availability and preferences of designated healthcare personnel.

Reference throughout this specification to "an example" means that a particular feature, structure, or characteristic described in connection with the example is included in at least one embodiment of the present invention. Thus, appearances of the phrase "in an example" in various places throughout this specification are not necessarily all referring to the same embodiment.

As used herein, a plurality of items, structural elements, compositional elements, and/or materials may be presented in a common list for convenience.

However, these lists should be construed as though each member of the list is individually identified as a separate and unique member. Thus, no individual member of such list should be construed as a de facto equivalent of any other member of the same list solely based on its presentation in a common group without indications to the contrary. In addition, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered illustrative and not restrictive, and the invention is not to be limited to the details given herein, but may be modified within the scope and equivalents of the appended claims.

Those having skill in the art will appreciate that many changes may be made to the details of the above-described embodiments without departing from the underlying principles of the invention. The scope of the present invention should, therefore, be determined only by the following claims.

What is claimed is:

1. A wearable medical monitoring device, comprising:

a microneedle array configured to extract interstitial or capillary fluid from a user;

a plurality of biosensors configured to detect a plurality of biomarkers from said extracted fluid, wherein said plurality of biomarkers includes glucose and at least one complete blood count parameter selected from a group consisting of white blood cells, red blood cells, hemoglobin, hematocrit, and platelet count;

microfluidic channels configured to transport said extracted fluid from said microneedle array to sensor chambers containing said plurality of biosensors, said microfluidic channels comprising flow rectifiers configured to maintain uniform fluid flow rates and heparin-coated anti-clotting surfaces configured to prevent sensor fouling;

a microprocessor coupled to said plurality of biosensors and configured to perform signal conditioning and pre-processing of biosensor signals and to generate biomarker data based on signals received from said plurality of biosensors; and a wireless communication module coupled to said microprocessor and configured to transmit said biomarker data to a user device for forwarding to a server, wherein said server comprises a cloud analytics layer configured to analyze said biomarker data using one or more machine learning models to detect anomalies indicative of health conditions, and an alerting and triage layer configured to generate a health alert based on a detected anomaly, said one or more machine learning models comprising:

a time-series forecasting model comprising a Long Short-Term Memory neural network configured to detect rate-of-change metrics for each biomarker and to predict biomarker trajectory based on detected trends;

an unsupervised anomaly detection model configured to detect rare patterns not present in training data;

a classification model configured to generate risk scores based on combinations of said at least one complete blood count parameter and metabolic markers; and an ensemble model configured to integrate outputs from said time-series forecasting model, said unsupervised anomaly detection model, and said classification model, and to require agreement across said models before generating said health alert, wherein said one or more machine learning models are configured to be updated via federated learning using anonymized data.

2. The wearable medical monitoring device of claim 1, wherein said plurality of biomarkers further comprises hemoglobin A1c.

3. The wearable medical monitoring device of claim 2, wherein said plurality of biomarkers further comprises prostate-specific antigen.

4. The wearable medical monitoring device of claim 1, wherein said microneedle array comprises microneedles measuring approximately 500-900 micrometers in length.

5. The wearable medical monitoring device of claim 1, further comprising a battery configured to provide power to said microprocessor and said wireless communication module, wherein said wearable medical monitoring device is configured for continuous operation for a period of up to thirty days without replacement.

6. A method for continuous health monitoring, said method comprising the steps of:

extracting, by a microneedle array of a wearable device adhered to skin of a user, interstitial or capillary fluid from said user;

transporting said extracted fluid through microfluidic channels from said microneedle array to sensor chambers, said microfluidic channels comprising flow rectifiers configured to maintain uniform fluid flow rates and heparin-coated anti-clotting surfaces configured to prevent sensor fouling;

detecting, by a plurality of biosensors of said wearable device, a plurality of biomarkers from said extracted fluid, wherein said plurality of biomarkers comprises glucose and at least one complete blood count parameter;

generating, by a microprocessor of said wearable device, biomarker data based on signals from said plurality of biosensors, wherein said microprocessor performs signal conditioning and pre-processing of said signals;

transmitting, by a wireless communication module of said wearable device, said biomarker data to a user device;

forwarding, by said user device, said biomarker data to a server via a network;

analyzing, by a cloud analytics layer of said server, said biomarker data using one or more machine learning models including at least one of a time-series forecasting model using Long Short-Term Memory neural networks configured to detect rate-of-change metrics for each biomarker and to predict biomarker trajectory based on detected trends, an unsupervised anomaly detection model configured to detect rare patterns not present in training data, a classification model for risk scoring, and an ensemble model configured to integrate outputs from said time-series forecasting model, said unsupervised anomaly detection model, and said classification model, and to require agreement across said models, to detect anomalies indicative of health conditions, wherein said one or more machine learning models are configured to be updated via federated learning using anonymized data; and generating, by an alerting and triage layer of said server, a health alert based on a detected anomaly.

7. The method of claim 6, wherein analyzing the biomarker data using said one or more machine learning models comprises applying the time-series forecasting model using Long Short-Term Memory neural networks to detect rate-of-change metrics for each biomarker and to predict biomarker trajectory based on said detected rate-of-change metrics.

8. The method of claim 7, further comprising predicting, by said server, a biomarker trajectory based on said detected rate-of-change metrics and generating a predictive health alert with an estimated time to threshold crossing when the predicted trajectory crosses a clinical threshold.

9. The method of claim 6, further comprising:

collecting, by said server, initial biomarker readings over a calibration period;

establishing, by said server, individualized baseline values for the at least one complete blood count parameter based on said initial biomarker readings; and adjusting, by said server, alert thresholds based on user-specific factors including age, sex, and known medical conditions.

10. The method of claim 9, further comprising:

detecting, by said server, an environmental context change based on environmental data received from the user device; and dynamically updating, by said server, said alert thresholds based on the detected environmental context change.

11. The method of claim 6, further comprising:

classifying, by said server, said detected anomaly by priority level;

transmitting, by said server, an immediate alert to a healthcare personnel device when said detected anomaly is classified as high priority; and providing, by said server, an artificial intelligence (AI)-annotated clinical summary along with trend graphs to the healthcare personnel device.

12. The method of claim 11, wherein classifying the detected anomaly by priority level comprises assigning the detected anomaly to one of a low priority level for non-urgent deviations, a moderate priority level for significant but non-immediate issues, and a high priority level for acute changes with potential for rapid deterioration.

13. A health monitoring system, comprising:

a wearable medical monitoring device configured to be adhered to skin of a user, said wearable medical monitoring device comprising:

a microneedle array configured to extract interstitial or capillary fluid from said user;

a plurality of biosensors configured to detect a plurality of biomarkers including glucose and at least one complete blood count parameter from the extracted fluid;

microfluidic channels configured to transport said extracted fluid from said microneedle array to sensor chambers, said microfluidic channels comprising flow rectifiers configured to maintain uniform fluid flow rates and heparin-coated anti-clotting surfaces configured to prevent sensor fouling;

a microprocessor configured to perform signal conditioning and pre-processing of biosensor signals and to generate biomarker data based on signals from the plurality of biosensors; and a wireless communication module configured to transmit said biomarker data;

a first user device configured to receive said biomarker data from said wearable medical monitoring device and to forward said biomarker data via a network; and a server configured to receive said biomarker data from said first user device, said server comprising:

a cloud analytics layer configured to analyze said biomarker data using one or more machine learning models to detect anomalies indicative of health conditions, said one or more machine learning models comprising a time-series forecasting model comprising a Long Short-Term Memory neural network, an unsupervised anomaly detection model, a classification model for risk scoring, and an ensemble model configured to integrate outputs from said time-series forecasting model, said unsupervised anomaly detection model, and said classification model, and to require agreement across said models before generating alerts; and an alerting and triage layer configured to generate a health alert based on a detected anomaly, wherein said one or more machine learning models are configured to be updated via federated learning using anonymized data.

14. The health monitoring system of claim 13, further comprising a second user device configured to be operated by healthcare personnel, wherein said server is configured to transmit said health alert to said second user device when said detected anomaly is classified as high priority.

15. The health monitoring system of claim 14, wherein said server is configured to provide an artificial intelligence (AI)-annotated clinical summary to said second user device, said AI-annotated clinical summary including trend graphs and suggested ICD-10 codes corresponding to the detected anomaly.

16. The health monitoring system of claim 13, wherein said server is configured to establish individualized baseline values for said at least one complete blood count parameter based on initial biomarker readings collected over a calibration period and to adjust alert thresholds based on user-specific factors derived from user profile data.

* * * * *